(12) United States Patent
Thuring et al.

(10) Patent No.: US 8,779,158 B2
(45) Date of Patent: Jul. 15, 2014

(54) TRISUBSTITUTED PYRAZOLES AS ACETYLCHOLINE RECEPTOR MODULATORS

(75) Inventors: Johannes Wilhelmus John F. Thuring, Antwerp (BE); Gregor James MacDonald, Zoersel (BE); Wei Zhuang, Antwerp (BE)

(73) Assignee: Janssen Pharmaceutica NV, Beerse (BE)

( * ) Notice: Subject to any disclaimer, the term of this patent is extended or adjusted under 35 U.S.C. 154(b) by 318 days.

(21) Appl. No.: 12/991,119

(22) PCT Filed: May 8, 2009

(86) PCT No.: PCT/EP2009/055617
§ 371 (c)(1),
(2), (4) Date: Nov. 4, 2010

(87) PCT Pub. No.: WO2009/135944
PCT Pub. Date: Nov. 12, 2009

(65) Prior Publication Data
US 2011/0065683 A1     Mar. 17, 2011

(30) Foreign Application Priority Data
May 9, 2008   (EP) .................................... 08155991

(51) Int. Cl.
*A61K 31/4155* (2006.01)
*A01N 43/36* (2006.01)
*C07D 231/02* (2006.01)
*C07D 401/04* (2006.01)

(52) U.S. Cl.
USPC ..................... 548/364.4; 546/275.4; 514/338; 514/406

(58) Field of Classification Search
USPC .............. 548/364.4; 546/275.4; 514/338, 406
See application file for complete search history.

(56) References Cited

U.S. PATENT DOCUMENTS

| | | |
|---|---|---|
| 3,933,838 A | 1/1976 | Manghisi et al. |
| 6,187,797 B1 | 2/2001 | Pruitt et al. |
| 6,245,916 B1 | 6/2001 | Fauchere et al. |
| 6,569,874 B1 | 5/2003 | Pruitt et al. |
| 8,143,419 B2 | 3/2012 | Thuring et al. |
| 2004/0073029 A1 | 4/2004 | Pruitt et al. |
| 2004/0254236 A1 | 12/2004 | Dong et al. |
| 2005/0004134 A1 | 1/2005 | Tsutsumi et al. |
| 2006/0063756 A1 | 3/2006 | Salituro et al. |
| 2010/0216846 A1 | 8/2010 | Thuring et al. |
| 2010/0240707 A1 | 9/2010 | Thuring et al. |
| 2010/0324053 A1 | 12/2010 | Macdonald et al. |
| 2011/0269748 A1 | 11/2011 | Thuring et al. |
| 2012/0172354 A1 | 7/2012 | Macdonald et al. |
| 2012/0238561 A1 | 9/2012 | Macdonald et al. |

FOREIGN PATENT DOCUMENTS

| | | |
|---|---|---|
| EP | 0248523 | * 12/1987 |
| EP | 267986 A | 5/1988 |
| EP | 275312 A | 7/1988 |
| EP | 1205478 A | 5/2002 |
| EP | 1044970 | 1/2003 |
| EP | 1070708 A1 | 1/2004 |
| WO | 96/03392 A1 | 2/1996 |
| WO | 97/05131 A | 2/1997 |
| WO | 98/15543 A | 4/1998 |
| WO | 98/28282 A2 | 7/1998 |
| WO | 99/21555 A2 | 5/1999 |
| WO | 01/44207 A2 | 6/2001 |
| WO | 01/64674 A | 9/2001 |
| WO | 01/74793 A | 10/2001 |
| WO | 02/24200 A | 3/2002 |
| WO | 02/42298 A | 5/2002 |
| WO | 02/057240 | 7/2002 |
| WO | 03/015773 | 2/2003 |
| WO | 03/062215 | 7/2003 |
| WO | 03/094831 | 11/2003 |
| WO | 2004/096225 | 11/2004 |
| WO | 2004/110350 | 12/2004 |
| WO | 2005/012263 | 2/2005 |
| WO | 2005/051917 | 6/2005 |
| WO | 2006/064375 | 6/2005 |
| WO | 2005/070926 | 8/2005 |
| WO | 2006/047256 | 5/2006 |
| WO | WO 2007/031440 | 3/2007 |
| WO | WO 2007/118903 | 10/2007 |
| WO | 2009/127678 | 10/2009 |
| WO | 2012/113850 | 8/2012 |

OTHER PUBLICATIONS

International Search Report for PCT/EP2009/055617 dated Aug. 11, 2009.
Written Opinion for PCT/EP2009/055617 dated Aug. 11, 2009.
Muccioli et al., Expert Opinion on Therapeutic Patents, Informa Healthcare, GB, vol. 16, No. 10 (2006), pp. 1405-1423.
Banerjee, Carolin et al., "Cellular Expression of α7 Nicotinic Acetylcholine Receptor Protein in the emporal Cortex in Alzheimer's and Parkinson's Disease—A Stereological Approach", Neurobiology of Disease, (2000), pp. 666-672, vol. 7.
Bickford, Paula C. et al., "Restoration of sensory gating of auditory evoked response by nicotine in fimbria-fornix lesioned rats", Brain Research, (1995), pp. 235-240, vol. 705.

(Continued)

*Primary Examiner* — Yong Chu
*Assistant Examiner* — Sonya Wright
(74) *Attorney, Agent, or Firm* — Peter Herridge

(57) ABSTRACT

The present invention relates to 1-alkyl-3-aniline-5-aryl-pyrazole derivatives and pharmaceutically acceptable salts thereof, processes for preparing them, pharmaceutical compositions containing them and their use in therapy, according to Formula (I).

The invention particularly relates to positive allosteric modulators of nicotinic acetylcholine receptors, such positive allosteric modulator having the capability to increase the efficacy of nicotinic receptor agonists.

7 Claims, No Drawings

(56) References Cited

OTHER PUBLICATIONS

Brown, D.J. et al., "The Chemistry of heterocyclic compounds: Fused Pyrimidines", Book—The Chemistry of Heterocyclic compounds, (1971), pp. 261-304, Chapter IV.
Burghaus, Lothar et al., "Quantitative assessment of nicotinic acetylcholine receptor proteins in the cerebral cortex of Alzheimer patients", Molecular Brain Research, (2000), pp. 385-388, vol. 76.
Chen et al., "1-Alkyl-3-amino-5-aryl-1H-[1,2,4]triazoles: Novel Synthesis Via Cyclization of N-Acyl-S-methylisothioureas with Alkylhydrazines and Their Potent Corticotropic-Releasing Factor-1 (CRF1) Receptor Antagonist Activities", Bioorganic & Medicinal Chemistry Letters, vol. 11, pp. 3165-3168 (2001).
Dalack, Gregory W. et al., "Nicotine Dependence in Schizophrenia: Clinical Phenomena and Laboratory Findings", Am J Psychiatry, Nov. 1998, pp. 1490-1500, vol. 155:11.
Dani, John A. et al., "Variations in desensitization of nicotinic acetylcholine receptors from hippocampus and midbrain dopamine areas", European Journal of Pharmacology, (2000), pp. 1-38, vol. 393.
Freedman, Robert et al., "Evidence in Postmortem Brain Tissue for Decreased Numbers of Hippocampal Nicotinic Receptors in Schizophrenia", Biol Psychiatry, (1995), pp. 22-33, vol. 38.
Freedman, Robert et al., "Linkage of a neurophysiological deficit in schizophrenia to a chromosome 15 locus", Proc. Natl. Acad. Sci. USA, Jan. 1997, pp. 587-592, vol. 94.
Gol'din et. al. Hcaplus Abstract 1974:437516, "Synthesis of triazolones and C-aminotriazoles by the thermal condensation of carbamidoamidrazones", 1974.
Grant, Morris, Guillory (in Brittain ed.), "Polymorphism, etc.," NY: Marcel Dekker, Inc., 1999, 1-2, 125-181, 183-226.
Griffith, Jay M. et al., "Nicotinic Receptor Desensitization and Sensory Gating Deficits in Schizophrenia", Biol Psychiatry, 1998, pp. 98-106, vol. 44.
Guan, Zhi-Zhong et al., "Decreased protein level of nicotinic receptor $\alpha 7$ subunit in the frontal cortex from schizophrenic brain", NeuroReport, Jun. 3, 1999, pp. 1779-1782, vol. 10 No. 8.
Hamill, O. P. et al., "Improved Patch-Clamp Techniques for High-Resolution Current Recording from Cells and Cell-Free Membrane Patches", Pflugers Arch, (1981) pp. 85-100, vol. 391.
Intelihealth, "Alzheimer's disease," online, accessed Jun. 30, 2008, http://www.intelihealth.com/IH/intlhIWSIHWOOO/8303/9117/195703.html?d=dmtHealthAZ.
Intelihealth, "Dementia," online, accessed Sep. 22, 2009, http://www.intelihealth.com/IH/ihtIHIWSIHWOOO/24479/11184.html.
Intelihealth, "Parkinson's disease," online, accessed Sep. 22, 2009, http://www.intelihealth.com/IH/ihtIH?d=dmtHealthAZ&c=201957.
Intelihealth, "Schizophrenia" online, accessed Oct. 4, 2011, http://www.intelihealth.com/IH/ihtIHIWSIHWOOO/8271/8694/1 8801 O.html?d=dmtHealthAZ#prevent.
Leonard, Sherry et al., "Association of Promoter Variants in the $\alpha 7$ Nicotinic Acetylcholine Receptor Subunit Gene With an Inhibitory Deficit Found in Schizophrenia", Arch Gen Psychiatry, Dec. 2002, pp. 1085-1096, vol. 59.
Lin et. al., "Recent developments in neuronal nicotinic acetycholine receptor modulators", 1998, 8 (8), pp. 991-1015.
Makara et al., "Solid-Phase Synthesis of 3-Alkylamino-1,2,4-triazoles", Organic Letters, vol. 4, No. 10, pp. 1751-1754 (2002).
Marutle, Amelia et al., "Laminar distribution of nicotinic receptor subtypes in cortical regions in schizophrenia", Journal of Chemical Neuroanatomy, (2001), pp. 115-126, vol. 22.
Muccioli, et al., "Latest Advances in Cannadinoid Receptor Antagonists and Inverse Agonists", Expert Opinion on Therapeutic Patents, vol. 16, No. 10, pp. 1405-1423, (2006).
Nagamatsu, Tomohisa et al., "General syntheses of -alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans., 2001, pp. 130-137.
Nagamatsu, Tomohisa et al., "Syntheses of 3-Substituted 1-Methyl-6-phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).
Ray, M.A. et al., "Neuronal nicotinic acetylcholine receptor subunits in autism: An immunohistochemical investigation in the thalamus", Neurobiology of Disease, (2005), pp. 366-377, vol. 19.
Ridley, Diana L. et al., "Differential effects of chronic drug treatment on $\alpha 3^*$ and $\alpha 7$ nicotinic receptor binding sites, in hippocampal neurons and SH-SY5Y cells", British Journal of Pharmacology, (2001), pp. 1286-1295, vol. 133.
Silverman, R. "The Organic Chemistry of Drug Design and Drug Action," 2004, Elsevier, pp. 29-32.
Stetter, Hermann et al., The Catalyzed Nucleophilic Addition of Aldehydes to Electrophilic Double Bonds, Organic Reactions, (1991), pp. 407-496, vol. 40, Chapter 4.
Vippagunta, et al., "Crystalline Solids", Advanced Drug Delivery Reviews, vol. 48, pp. 3-26, (2001).
Virginio, Caterina et al., "Pharmacological properties of rat $\alpha 7$ nicotinic receptors expressed in native and recombinant cell systems", European Journal of Pharmacology, (2002), pp. 153-161, vol. 445.
West, Anthony R., Solid State Chemistry and its Applications, Wiley, New York, 1988, pp. 358 & 365.
Yu et al., "Physical characterization of, etc.," PSTT, vl. 1(3), 118-127 (1998).
Office Action mailed Aug. 12, 2011 in U.S. Appl. No. 12/063,689.
Office Action mailed Dec. 21, 2011 in U.S. Appl. No. 12/063,689.
Final Office Action mailed Apr. 5, 2012 in U.S. Appl. No. 12/063,689.
Notice of Allowance mailed Jul. 23, 2012 in U.S. Appl. No. 12/063,689.
Office Action mailed Oct. 13, 2011 in U.S. Appl. No. 12/738,763.
Office Action mailed Dec. 14, 2011 in U.S. Appl. No. 12/738,763.
Final Office Action mailed Apr. 19, 2012 in U.S. Appl. No. 12/738,763.
Notice of Allowance mailed Aug. 9, 2012 in U.S. Appl. No. 12/738,763.
Notice of Allowance mailed Jan. 17, 2013 in U.S. Appl. No. 12/738,763.
Office Action mailed Dec. 2, 2011 in U.S. Appl. No. 12/738,725.
Notice of Allowance mailed Apr. 4, 2012 in U.S. Appl. No. 12/738,725.
Notice of Allowance mailed Jul. 19, 2012 in U.S. Appl. No. 12/738,725.
Office Action mailed May 2, 2012 in U.S. Appl. No. 12/866,054.
Office Action mailed Aug. 10, 2012 in U.S. Appl. No. 12/866,054.
Final Office Action mailed Feb. 22, 2013 in U.S. Appl. No. 12/866,054.

* cited by examiner

TRISUBSTITUTED PYRAZOLES AS ACETYLCHOLINE RECEPTOR MODULATORS

CROSS REFERENCE TO RELATED APPLICATIONS

This application claims priority from and is the national stage of PCT Application No. PCT/EP2009/055617, filed May 8, 2009, which claims priority from European Patent Application No. 08155991.6, filed May 9, 2008, the entire disclosures of which are hereby incorporated in their entirety.

The present invention relates to 1-alkyl-3-aniline-5-aryl-pyrazole derivatives and pharmaceutically acceptable salts thereof, processes for preparing them, pharmaceutical compositions containing them and their use in therapy. The invention particularly relates to positive allosteric modulators of nicotinic acetylcholine receptors, such positive allosteric modulators having the capability to increase the efficacy of nicotinic receptor agonists.

BACKGROUND PRIOR ART

W0-2007/118903 discloses 1-alkyl-3-aniline-5-aryl-1,2,4-triazoles as positive modulators of nicotinic acetylcholine receptors useful for treating neurological, degenerative and psychiatric disorders.

EP-0,248,523 discloses N-[4-methoxyphenyl)-1-methyl-5-phenyl-1H-pyrazol-3-amine useful as a broad spectrum anti-inflammatory agent.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit and memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, bipolar disorder, Parkinson's disease, Huntington's disease, Tourette's syndrome, brain trauma and other neurological, degenerative and psychiatric disorders in which there is loss of cholinergic synapses, including jetlag, nicotine addiction, and pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and of particular note at the α7-nicotinic receptor, desensitization limits the duration of action of an applied agonist.

DESCRIPTION OF THE INVENTION

We have found that certain novel pyrazole derivatives can increase the efficacy of agonists at nicotinic acetylcholine receptors (nAChR). Compounds having this type of action (hereinafter referred to as "positive allosteric modulators") are likely to be useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur with prolonged application of agonists.

Positive nAChR modulators of the present invention are useful for treatment and prophylaxis of psychotic disorders, intellectual impairment disorders and diseases, inflammatory diseases and conditions in which modulation of the α7 nicotinic receptor is beneficial.

The present invention concerns 1-alkyl-3-aniline-5-aryl-pyrazole derivatives having positive allosteric modulator properties, in particular increasing the efficacy of agonists at the α7 nicotinic receptor. The invention further relates to methods for their preparation and pharmaceutical compositions comprising them. The invention also relates to the use of these derivatives for the manufacture of a medicament for the treatment and prophylaxis of psychotic disorders, intellectual impairment disorders and diseases, inflammatory diseases and conditions in which modulation of the α7 nicotinic receptor is beneficial.

The compounds of the present invention differ structurally from the prior art compounds.

The present invention relates to a compound according to formula (I)

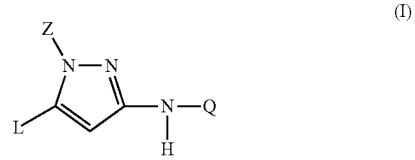

or a stereochemically isomeric form thereof, wherein
Z is $C_{1-6}$alkyl substituted with one or more substituents independently selected from the group consisting of hydroxyl, $R^1R^2N—C(=O)—$, $R^3O—C(=O)—$ and halo;
Q is 2,2-difluorobenzodioxol-5-yl, unsubstituted phenyl or phenyl substituted with one, two or three substituents independently selected from the group consisting of halo, hydroxyl, cyano, $C_{1-6}$alkyl, $C_{1-6}$alkyl-O—, polyhalo$C_{1-6}$alkyl and polyhalo$C_{1-6}$alkyl-O—;

L is phenyl, pyridinyl or benzodioxanyl, each optionally substituted with one, two or more substituents independently selected from the group consisting of halo, cyano, $C_{1-6}$alkyl, $C_{1-6}$alkyl-O—, $C_{1-6}$alkyl-S—, polyhalo$C_{1-6}$alkyl, polyhalo$C_{1-6}$alkyl-O—, mono- and di($C_{1-6}$alkyl)amino, pyrrolidinyl, piperidinyl, morpholinyl, $CH_3O$—$C_{1-6}$ alkyl-NH—, HO—$C_{1-6}$alkyl-NH—, $C_{3-6}$cycloalkyl, $C_{3-6}$cycloalkyl-NH—, $C_{3-6}$cycloalkyl$C_{1-6}$alkyl-NH—, methoxycarbonyl, $C_{1-6}$alkyl-O—$C_{1-6}$alkyl- and $C_{3-6}$cycloalkyl-O—$C_{1-6}$alkyl-;

$R^1$ and $R^2$ each independently represent hydrogen, $C_{1-6}$alkyl, $C_{3-6}$cycloalkyl, $C_{1-4}$alkyl-O—$C_{1-6}$alkyl or $C_{3-6}$cycloalkyl$C_{1-6}$alkyl; or $R^1$ and $R^2$ taken together with the nitrogen atom to which they are attached form a heterocyclic radical selected from the group consisting of pyrrolidinyl, piperidinyl, and morpholinyl, each optionally substituted with one, two or three substituents each independently selected from the group consisting of halo, hydroxy and $C_{1-6}$alkyl;

$R^3$ is hydrogen or $C_{1-3}$alkyl; or a pharmaceutically acceptable addition salt, or a hydrate or a solvate thereof.

The present invention relates in particular to a compound according to formula (I) or a stereoisomeric form thereof, wherein Z is $C_{1-4}$alkyl substituted with hydroxyl or $R^1R^2N$—C(=O)—;

Q is 2,2-difluorobenzodioxol-5-yl, phenyl substituted with one, two or three substituents independently selected from the group consisting of halo, trifluoromethyl, trifluoromethoxy, and methoxy;

L is phenyl substituted with one or two substituents selected from the group consisting of halo and methoxy; pyridinyl substituted with one, two or three substituents selected from the group consisting of halo, methyl, $C_{1-2}$alkylamino, $C_{1-2}$alkyloxycarbonyl, and $C_{1-2}$alkyloxy$C_{1-2}$alkyl; or benzodioxanyl;

$R^1$ and $R^2$ each independently represent hydrogen, $C_{1-4}$alkyl, $C_{3-6}$cycloalkyl or $C_{3-6}$cycloalkyl$C_{1-3}$alkyl; or a pharmaceutically acceptable addition salt, or a hydrate or a solvate thereof.

The present invention more particularly relates to a compound of Formula (I) or a stepreoisomeric form thereof, wherein L is pyridinyl substituted with one or two substituents selected from the group consisting of halo, methyl, $C_{1-2}$alkylamino, $C_{1-2}$alkyloxycarbonyl, and $C_{1-2}$alkyloxy$C_{1-2}$alkyl; or benzodioxanyl;

$R^1$ and $R^2$ each independently represent hydrogen, methyl, ethyl, cyclopropyl, cyclobutyl or cyclopropylmethyl; or a pharmaceutically acceptable addition salt, or a hydrate or a solvate thereof.

The present invention relates in particular to a compound according to formula (I) or a stereoisomeric form thereof, wherein Z is (2S)-2-hydroxypropyl, (2S)-2-hydroxybutyl, $(CH_3)_2N$—C(=O)—$CH_2$—$CH_2$—, $CH_3NH$—C(=O)—$CH_2$—, $C_2H_5NH$—C(=O)—$CH_2$—, c.$C_3H_5NH$—C(=O)—$CH_2$—, c.$C_3H_5$—$CH_2$—NH—C(=O)—$CH_2$—, or c.$C_4H_7NH$—C(=O)—$CH_2$—, Q is 2,2-difluorobenzodioxol-5-yl, phenyl substituted with one, two or three substituents independently selected from the group consisting of fluoro, chloro, trifluoromethyl, trifluoromethoxy, and methoxy;

L is 4-pyridinyl substituted with one or two substituents selected from the group consisting of chloro, methyl, methylamino, ethylamino, dimethylamino, methoxycarbonyl and methoxymethyl;

or a pharmaceutically acceptable addition salt, or a hydrate or a solvate thereof.

The present invention relates in particular to a compound according to formula (I) or a stereoisomeric form thereof, wherein Z is (2S)-2-hydroxypropyl, (2S)-2-hydroxybutyl, $(CH_3)_2N$—C(=O)—$CH_2$—$CH_2$—, $CH_3NH$—C(=O)—$CH_2$—, $C_2H_5NH$—C(=O)—$CH_2$—, c.$C_3H_5NH$—C(=O)—$CH_2$—, c.$C_3H_5$—$CH_2$—NH—C(=O)—$CH_2$—, or c.$C_4H_7NH$—C(=O)—$CH_2$—, Q is 2,2-difluorobenzodioxol-5-yl, phenyl substituted with one, two or three substituents independently selected from the group consisting of fluoro, chloro, trifluoromethyl, trifluoromethoxy, and methoxy;

L is 4-methoxyphenyl or benzodioxanyl;

or a pharmaceutically acceptable addition salt, or a hydrate or a solvate thereof.

It will be appreciated that some of the compounds according to formula (I) and the addition salts, hydrates and solvates thereof may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The term solvates refers to alcoholates which the compounds according to formula (I) as well as the salts thereof, may form.

Some of the compounds according to formula (I) may also exist in their tautomeric form. Such forms although not explicitly indicated in the above formula are intended to be included within the scope of the present invention.

Preparation of the Compounds

A compound according to the invention can generally be prepared by a succession of steps, each of which is known to the skilled person. In particular, the compounds in this patent application can be prepared according to one or more of the following preparation methods. In the following schemes, and unless otherwise indicated, all variables are used as defined in Formula (I).

Scheme 1

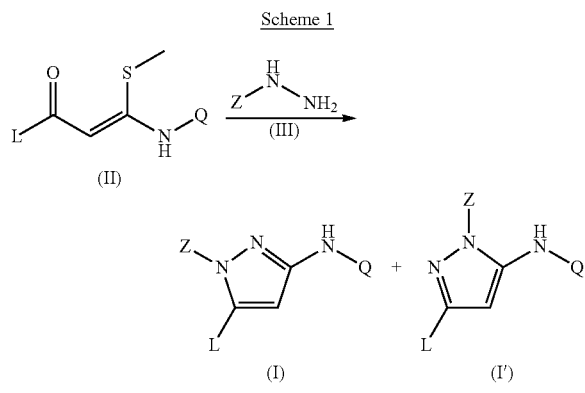

The compounds of this invention can be prepared by any of several standard synthetic processes commonly used by those skilled in the art of organic chemistry and are generally prepared according to Scheme 1 by transforming an 3-N-substituted 3-(methylthio)-1-arylprop-2-en-1-one derivative of general formula (II) into the pyrazoles of formula (I) using an appropriate hydrazine (III) under art known conditions. This transformation is typically performed in a protic solvent, such as an alcohol, in particular a branched alcohol, such as tert butyl alcohol at a temperature between room temperature and 180° C., in particular between 90° C. and 160° C. Alternatively, said transformation may be successfully carried out in an aprotic solvent, such as THF or the like, at a temperature between room temperature and 180° C., in particular between 100° C. and 160° C., optionally in a pressure tube or autoclave. Said reaction usually generates a mixture of two regioisomers with the aniline function either at the 3-position, such as in (I), or at the 5-position, such as in (I'). The ratio at which said isomers (I) and (I') are formed depends on several factors, such as the concentration of the reactants and solvent and in particular on the nature of the 2-propen-1-one (I) and the hydrazine (III). The addition of a Lewis acid may offer advantages, such as lowering the reaction temperature, and also effects the isomeric ratio of (I) and (I'). Examples of successful applications of the use of a Lewis acid are, but are not limited to, $ZnCl_2$ in THF, and lanthanum(III) triflate in tert butyl alcohol. In certain cases when the hydrazine (III) is used as a hydrochloric acid salt, the use of a stoichiometric amount of a tertiary amine base, such as diisopropylethyl amine, or the like, may be advantageous.

The synthesis of 3-N-substituted 3-(methylthio)-1-arylprop-2-en-1-one derivatives of general formula (II) can be effected by different synthetic routes, the success of which is dependent on the nature of the substrate, in particular the aryl group L. In a first embodiment, as illustrated in Scheme 2, an acetyl containing building block of the general formula (IV) is reacted with an aryl thioisocyanate of the general formula (V). Said reaction involves in situ deprotonation of the acetyl function with a strong inorganic base, such as sodium hydride, or the like, in an aprotic solvent, such as DMF or the like, in a temperature range between −20° C. and 40° C., preferably at 0° C. The addition of the aryl thioisocyanate of the general formula (V) to the in situ generated enolate, as described hereinbefore, is carried out between −20° C. and 40° C., preferably at 0° C. The thus obtained addition product can then be trapped in situ by addition of methyl iodide at a temperature range between 0° C. and 40° C., preferably at room temperature, to afford the 3-N-substituted 3-(methylthio)-1-arylprop-2-en-1-one derivative of the general formula (II). Intermediates of Formula (II) may also exist in the tautomeric form (II-a), each in an E or Z configuration or a mixture thereof (Scheme 2).

Scheme 2

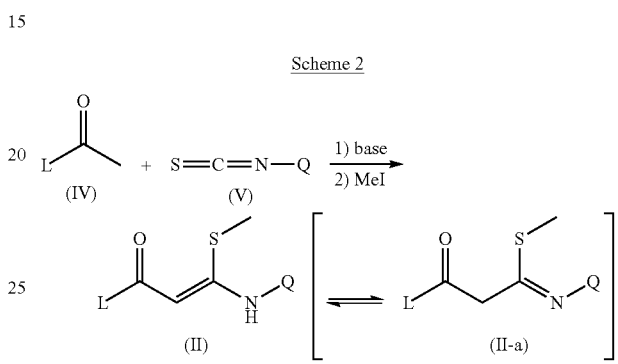

In a second embodiment, which comprises two separate synthetic steps, as illustrated in Scheme 3, an acetyl containing building block of the general formula (IV) is reacted with carbon disulfide. Said reaction involves prior deprotonation of the acetyl function with a strong inorganic base, such as sodium hydride, or the like, in an aprotic solvent, such as DMF or the like, at a temperature range between −20° C. and 40° C., preferably at 0° C. The addition of carbon disulfide to the in situ generated enolate, as described hereinbefore, is carried out between −20° C. and 40° C., preferably at 0° C. The thus obtained addition product can then be trapped in situ by addition of methyl iodide at a temperature range between 0° C. and 40° C. to afford the intermediate of the general formula (VI). In a second step, the intermediate of the general formula (VI) is treated with an aniline, $H_2N$-Q, in an apolar solvent, such as toluene, or the like, and is most advantageously carried out at elevated temperatures, such as 110° C. The use of a Lewis acid catalyst is preferred, and may be, but is not limited to, boron trifluoride etherate.

Scheme 3

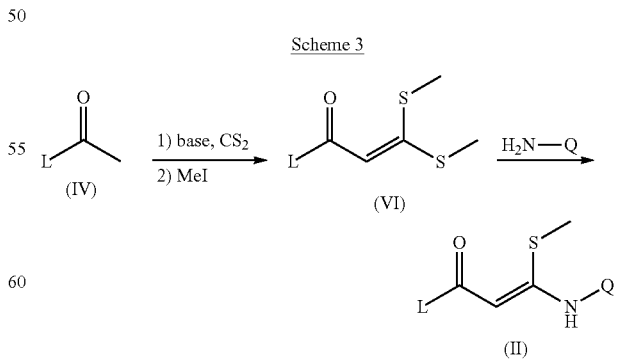

The synthesis of an acetyl substituted intermediate of the general formula (IV) can be effected starting from an aromatic nitrile L-CN (Scheme 3a). Said nitrile is treated with a Grignard reagent, such as Me-MgBr, in an aprotic solvent such as diethyl ether, or the like. An acceptable temperature range to effect said transformation is between 0° C. and 40° C., preferably at room temperature. One skilled in the art will recognize that this reaction will yield the corresponding imine of (IV), and that a subsequent aqueous hydrolysis step in diluted acid will afford the acetyl substituted intermediate of the general formula (IV).

Scheme 3a

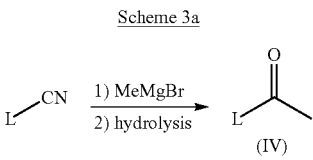

The hydrazine alcohols of the general formula (III-a), herein named (VIII), can be prepared from a mono-substituted oxirane of the general formula (VII) wherein $R^4$ represents $C_{1-4}$alkyl by heating in an excess of hydrazine hydrate (Scheme 4). Preferably the reaction temperature is 40-70° C. and the reaction time is 2 hours. If the oxirane (VII) is available in optically pure form, the resulting hydrazine alcohol (VIII) is obtained with the corresponding stereochemical identity and purity, such as for example when $R^4$ is ethyl.

Scheme 4

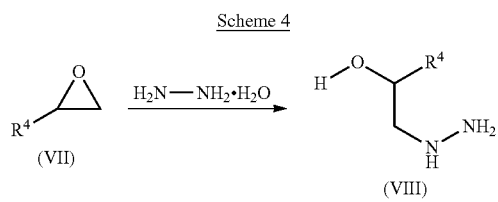

Several compounds of the general formula (I) can be obtained by functional group transformations involving the substituents L and Z. Scheme 5 represents an example of said functional group transformation, involving the substituent Z in a compound of the general formula (I). In particular, Scheme 5 represents the preparation of carboxylic acid amides of the general formula (Ib) from the corresponding carboxylic acid esters (Ia) wherein $R^3$ represents $C_{1-3}$alkyl involving the treatment with a primary or secondary aliphatic amine $HNR^1R^2$. In one embodiment, said transformation can be effected directly from the ester (Ia). A preferred solvent is a protic solvent, such as a lower alkyl alcohol, for instance methanol or the like. The preferred reaction temperature is between room temperature and 120° C.

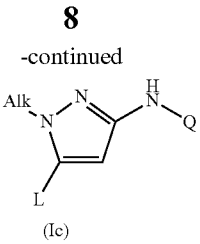

(Ic)

Alternatively, the alkyl carboxylic acid ester (Ia) is first hydrolyzed to yield the corresponding carboxylic acid of the general formula (Ic). This transformation can be effected by using a metal hydroxide (M-OH), such as potassium hydroxide, or more preferably lithium hydroxide. The reaction is performed in an aqueous environment, and is most advantageously carried out in the presence of at least one, or more preferably two water miscible organic co-solvents, such as THF and methanol, or the like. Further conversion of the carboxylic acid (Ic) into the amides of formula (Ib) is done using art known procedures, such as for example the treatment with a primary or secondary amine $HNR^1R^2$ as defined hereinbefore in the presence of a conventional amide coupling reagent such as HBTU (O-benzotriazole-N,N,N',N'-tetramethyl uronium hexafluorophosphate), EDCI, or EDAC in an aprotic solvent like $CH_2Cl_2$, or more preferably in a polar aprotic solvent like THF or DMF in the presence of an amine base additive, such as diisopropyl ethyl amine. Under certain circumstances the use of HOBT as an additive is an advantage.

Schemes 6-8 represent examples of functional group transformations involving the substituent L in a compound of the general formula (I). In a first example of said substituent L modification, as depicted in Scheme 6, the reductive removal of a chlorine atom in a structure of the general formula (Id) can be achieved catalytically, under a hydrogen atmosphere and using Pd/C as the catalyst, in the presence of an inorganic base, such as potassium acetate, or an amine base, such as triethyl amine, or the like. Alternatively, when either of the substituents Z and Q contain functionalities that are not compatible with catalytic hydrogenation conditions, the target compound of the general formula (Ie) can be obtained from the chloro pyridine of the general formula (Id) wherein $R^5$, $R^6$ and $R^7$ independently represent hydrogen or $C_{1-6}$alkyl, by treatment with a carbenoid catalyst, such as the Pd catalyst [1,3-bis[2,6-bis(1-methylethyl)phenyl]-2-imidazolidinylidene]chloro(η3-2-propenyl)-palladium ([478980-01-7]), in the presence of a strong base, such as sodium methoxide in a protic solvent, such as methanol or 2-propanol, or the like. Said reaction can be carried out at elevated temperature, such as 100-120° C. in a microwave oven (Scheme 6).

Scheme 5

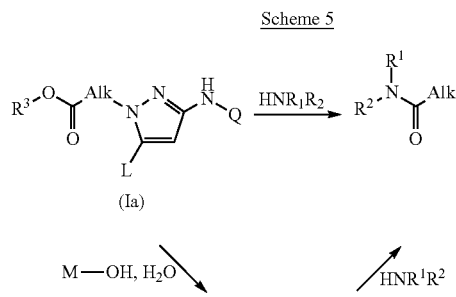

Scheme 6

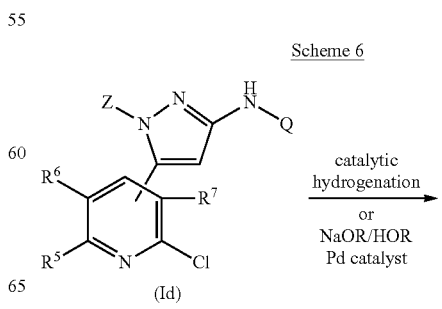

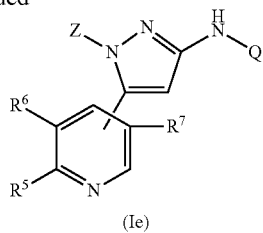

In a second example of substituent L modification as depicted in Scheme 7, the displacement of a chlorine atom in a structure of the general formula (Id) can be achieved by treatment of a chloro substituted pyridinyl pyrazole of the general formula (Id) with a $C_{1-6}$alkylamine in an alcoholic solvent, such as ethanol or the like, and heating at high temperatures, preferably at 100-200° C. in a pressure tube or microwave oven (Scheme 7).

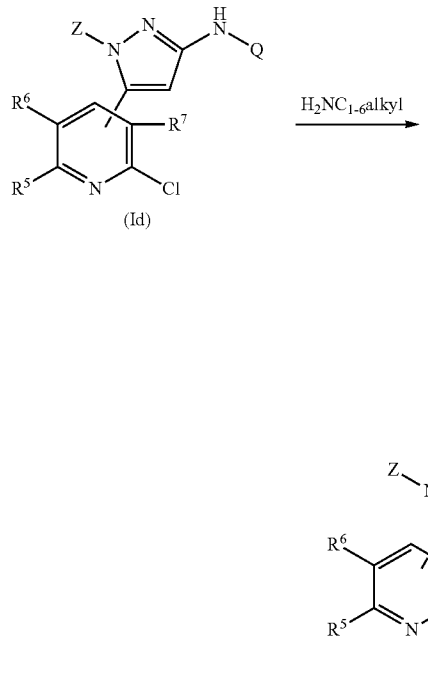

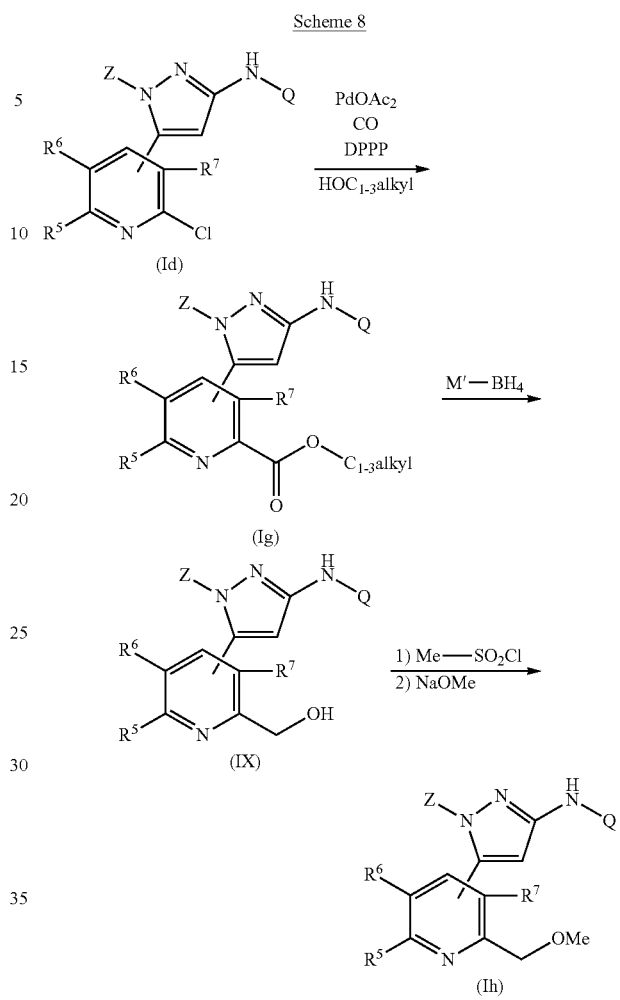

In a third example of substituent L modification as depicted in Scheme 8, the introduction of a methoxy methyl substituent can be achieved in a sequence involving three synthetic steps starting from a chloro substituted pyridinyl pyrazole of the general formula (Id). In a first step the alkyl carboxylate of the general formula (Ig) can be obtained from the chloro pyridinyl precursor (Id) through a CO insertion reaction. Suitable conditions are the use of palladium acetate in the presence of a ligand, such as 1,3-bis(diphenylphosphinopropane (DPPP), under a CO atmosphere at a pressure of 50 atm, and an inorganic base such as potassium acetate or the like. The reaction further requires a polar solvent, such as THF or the like, and an alcoholic co-solvent. When $C_{1-3}$alkyl is methyl, the co-solvent should be methanol. The reaction is best performed at high temperature, such as between 120° C. and 150° C.

In a second step, the hydroxylmethyl compound of the general formula (IX) can be obtained by treatment of the alkyl carboxylate (Ig) with a reductant, such as lithium borohydride or sodium borohydride in the presence of calcium chloride. The reaction can be advantageously carried out in a temperature range between 0° C. and room temperature, in a mixture of solvents consisting of an aprotic solvent, such as THF or the like, and a protic solvent, such as methanol or the like. In a third step the primary hydroxyl function in a structure of the general formula (IX) can be functionalized as a methane sulfonate, involving the use of a tertiary amine base, such as triethyl amine, or the like, and methane sulfonyl chloride in an aprotic solvent, such as THF or the like, at room temperature. Said methane sulfonate is trapped in situ by sodium methoxide in methanol as a solvent, to afford a compound of the general formula (Ih). It will be recognized by someone skilled in the art that, during the execution of the reaction sequence shown in Scheme 8, a protecting group is required if either one or both substituents Z and Q contain functionalities that are not compatible with the reaction conditions used in Scheme 8. For instance, when Z contains a hydroxyl function, said hydroxyl can be protected with a silyl function, such as tert-butyl dimethylsilyl or the like using art known conditions. Said silyl protecting group can be removed at the end of the sequence shown in Scheme 8 in the presence of tetrabutyl ammonium fluoride using art known conditions.

In another embodiment, compounds of the present invention can be prepared through a process that involves functionalisation of the N-1 atom of an intermediate of the general formula (X), as is outlined in Scheme 9. Said strategy is especially useful in cases where a hydrazine reagent of the general formula (III) is not readily available.

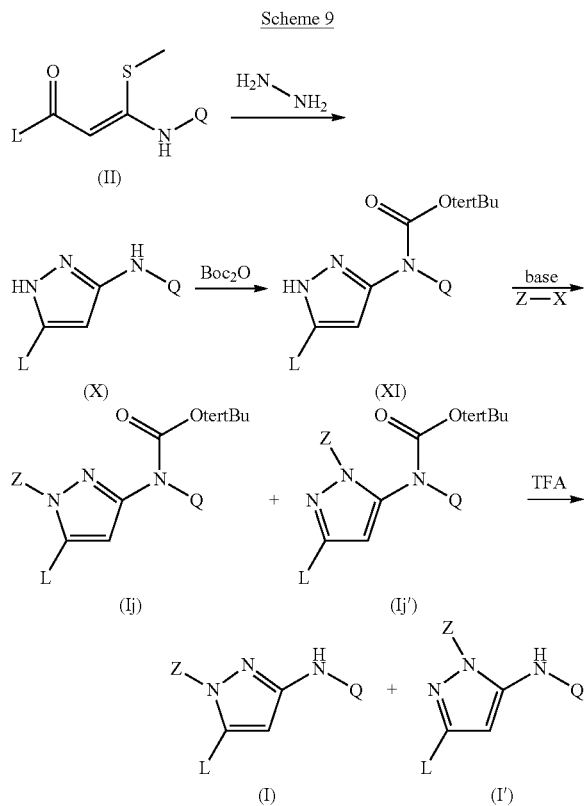

Scheme 9

In a first step an intermediate of the general formula (X) is prepared by reacting a 3-N-substituted 3-(methylthio)-1-arylprop-2-en-1-one derivative of general formula (II) with hydrazine. This transformation is typically performed in a protic solvent, such as an alcohol, in particular a branched alcohol, such as tert butyl alcohol or the like at a temperature between room temperature and 180° C., in particular between 90° C. and 120° C. In a second step the aniline amino function is protected by using a protecting group that is commonly applied by one skilled in the art. In particular, a tert-butoxycarbonyl (Boc) group can be advantageously used. To obtain the protected pyrazole of the general formula (XI), said Boc group can be introduced by deprotonation of the pyrazole of the general formula (X) using a strong inorganic base, such as sodium hydride or the like, in an aprotic solvent, such as DMF or the like, followed by quenching with Boc$_2$O. The preferred reaction temperature is between 0° C. and room temperature. In the third step of the synthetic sequence depicted in Scheme 9, the protected pyrazole of the general formula (XI) is treated with an alkylating agent Z—X wherein Z is as defined before and X represents a leaving group such as chloro, bromo or p-toluenesulfonate in the presence of an inorganic base, such as cesium carbonate, or the like, in an aprotic solvent, such as DMF or the like, at a temperature range between 0° C. and 70° C., to afford the protected pyrazoles as a mixture of regioisomers (Ij) and (Ij'). The final deprotection step is performed under art known conditions, specifically by treatment with trifluoro acetic acid, in a halogenated co-solvent, such as dichloro methane, or the like, at room temperature, to afford the compounds of the general formula (I) and (I').

Pharmacology

The compounds of the present invention were found to be positive allosteric modulators of the α7 nicotinic receptor. The α7 nicotinic receptor (α7 nAChR) belongs to the superfamily of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the α7 locus on 15q13-14 and polymorphisms in core promoter region of the α7 gene.

Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition, PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein, the PAM-induced increase in α7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 1-4, based on qualitative kinetic properties, as determined by whole-cell voltage-clamp recordings. This classification is based on the effect of an α7 PAM compound, as described hereinbefore, on the signal elicited by an agonist application. In particular, said agonist is choline at a concentration of 1 mM. In a preferred experimental setting, said α7 PAM compound and choline are simultaneously applied to the cell, as described hereinafter. Desensitization is defined as the closure of the receptor upon activation during the application of the agonist in whole-cell voltage-clamp electrophysiology measurements seen as the reduction of the outward current after initial activation by the agonist.

The definition of the PAM types 1-4 is described hereinafter:

Type 0 compounds minimally enhance the effect size of the current elicited by 1 mM choline.

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 µM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

A compound was considered to have interesting PAM-like activity when the potentiation of the peak current was at least 200% compared to the control choline response (=100%). Such compounds are classified as belonging to a particular PAM type in the Experimental Part. Compounds not meeting the condition are not classified as belonging to a particular PAM-type.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include

- 1,4-Diazabicyclo[3.2.2]nonane-4-carboxylic acid, 4-bromophenyl ester, monohydrochloride (SSR180711A);
- (−)-spiro[1-azabicyclo[2.2.2.]octane-3,5'-oxazolidine]-2'-one;
- 3-[(2,4-Dimethoxy)Benzylidene]-Anabaseine Dihydrochloride (GTS-21);
- [N-[(3R)-1-Azabicyclo[2.2.2]oct-3-yl]-4-chlorobenzamide Hydrochloride] PNU-282987;
- nicotine;
- varenicline;
- MEM3454;
- AZD-0328; and
- MEM63908.

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

The compounds may also find therapeutical use as anti-inflammatory medicines because the nicotinic acetylcholine receptor α7 subunit is essential for inhibiting cytokine synthesis by the cholinergic inflammatory pathway. Examples of indications which may be treated by the compounds are endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, post-operative ileus, pancreatitis, heart failure, acute lung injury and allograft rejection.

The compounds of the invention may find therapeutical use in the following indications as cognition in schizophrenia, cognition in Alzheimer' disease, mild cognitive impairment, Parkinson's disease, attention deficit hyperactivity disorder, ulcerative colitis, pancreatitis, arthritis, sepsis, postoperative ileus and acute lung injury.

In view of the above described pharmacological properties, the compounds according to formula (I) or any subgroup thereof, their, pharmaceutically acceptable addition salts, quaternary amines and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the α7 nicotinic receptor is beneficial.

In view of the utility of the compounds according to formula (I), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, a pharmaceutically acceptable addition salt, a solvate, or a quaternary amine thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered between 0.01 mg/kg to 2.50 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional α7 nicotinic receptor agonists, such as for example 1,4-Diazabicyclo[3.2.2]nonane-4-carboxylic acid, 4-bromophenyl ester, monohydrochloride (SSR180711A); (−)-spiro[1-azabicyclo[2.2.2]octane-3,5'-oxazolidine]-2'-one; 3-[(2,4-Dimethoxy)Benzylidene]-Anabaseine Dihydrochloride (GTS-21); [N-[(3R)-1-Azabicyclo[2.2.2]oct-3-yl]-4-chlorobenzamide Hydrochloride] PNU-282987; nicotine; varenicline; MEM3454; AZD-0328 and MEM63908. Thus, the present invention also relates to the combination of a compound according to formula (I) and a α7 nicotinic receptor agonist. Said combination may be used as a medicine. The present invention also relates to a product comprising (a) a compound according to formula (I), and (b) a α7 nicotinic receptor agonist, as a combined preparation for simultaneous, separate or sequential use in the treatment of diseases wherein modulation of the α7 nicotinic receptor is beneficial. The different drugs may be combined in a single preparation together with pharmaceutically acceptable carriers.

EXPERIMENTAL PART

Several methods for preparing the compounds of this invention are illustrated in the following Examples. Unless otherwise noted, all starting materials were obtained from commercial suppliers and used without further purification.

Hereinafter or hereinbefore, "THF" means tetrahydrofuran; "DMF" means N,N-dimethylformamide; "EtOAc" means ethyl acetate; "DMSO" means dimethylsulfoxide; "min" means minutes; "DMAA" means N,N-dimethyl-2-propenamide "MeOH" means methanol; "EtOH" means ethanol; "EtNH$_2$" means ethanamine; "Et$_2$O" means diethyl ether; "t-BuOH" means tert-butanol; "TBAF" means tetrabutylammonium fluoride; "TFA means trifluoroacetic acid "NH$_4$OAc" means ammonium acetate, "EDAC" means N3-(ethylcarbonimidoyl)-N$_1$,N$_1$-dimethyl-1,3-propanediamine, "EDCI" means N'-(ethylcarbonimidoyl)-N,N-dimethyl-1,3-propanediamine monohydrochloride, "HOBT" means 1-hydroxy-1H-benzotriazole, "Boc$_2$O" means di-tert-butyl dicarbonate and "Pd(OAc)$_2$ means palladium diacetate.

Microwave assisted reactions were performed in a single-mode reactor: Initiator™ Sixty EXP microwave reactor (Biotage AB), or in a multimode reactor: Micro-SYNTH Labstation (Milestone, Inc.).

The following examples are intended to illustrate but not to limit the scope of the present invention.

A. Preparation of the Intermediate Compounds

Description 1

2-Chloro-3-methyl-4-pyridinecarbonitrile (D1)

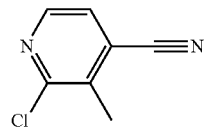

2-Chloro-3-methyl-4-pyridinecarboxylic acid (30 g; 174 mmol) was dissolved in pyridine (250 ml) and cooled to 0° C. Methanesulfonyl chloride (13.6 ml) was then added dropwise and the reaction mixture was stirred at 0° C. for 1 hour. NH$_3$ (gas) was added under pressure and the reaction mixture was stirred at room temperature for 1 h. After the reaction had reached completion, the excess NH$_3$ was removed in vacuo. The reaction mixture was then cooled to 0° C., methanesulfonyl chloride (140 ml) was added and the reaction mixture stirred at room temperature overnight. The mixture was then poured into 0.1 M HCl (200 ml) at 0° C. (with care), and adjusted to pH=7 with 1 M NaOH. The reaction mixture was extracted with EtOAc (2×100 ml), washed with brine, dried (MgSO$_4$), filtered and the solvent evaporated in vacuo. The residue was purified by flash column chromatography over silica gel (Biotage flash purification system; gradient: EtOAc/heptane from 15/85 to 30/70). The product fractions were collected and the solvent was evaporated in vacuo. Yield: 12.6 g of D1.

Description 2

1-(2-Chloro-3-methyl-pyridin-4-yl)-ethanone (D2)

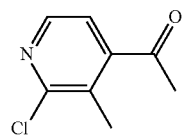

In a pre-dried flask, D1 (12.6 g; 82.9 mmol) was dissolved in Et$_2$O (anhydrous) (200 ml) and under N$_2$ (gas) protection, bromomethyl magnesium (100 ml) was added slowly. The reaction mixture was stirred at room temperature overnight and then poured slowly into a mixture of ice-H$_2$O (600 ml) and 37% aqueous HCl (100 ml). The reaction mixture was stirred and extracted with Et$_2$O (200 ml×4). The combined organic phases were then washed with brine, dried (Na$_2$SO$_4$), filtered and the solvent evaporated in vacuo. Yield: 11.6 g of D2 (88% pure product).

The following intermediates were also prepared by a procedure similar to that described in D1 and D2:

In a similar manner the following intermediates were prepared:

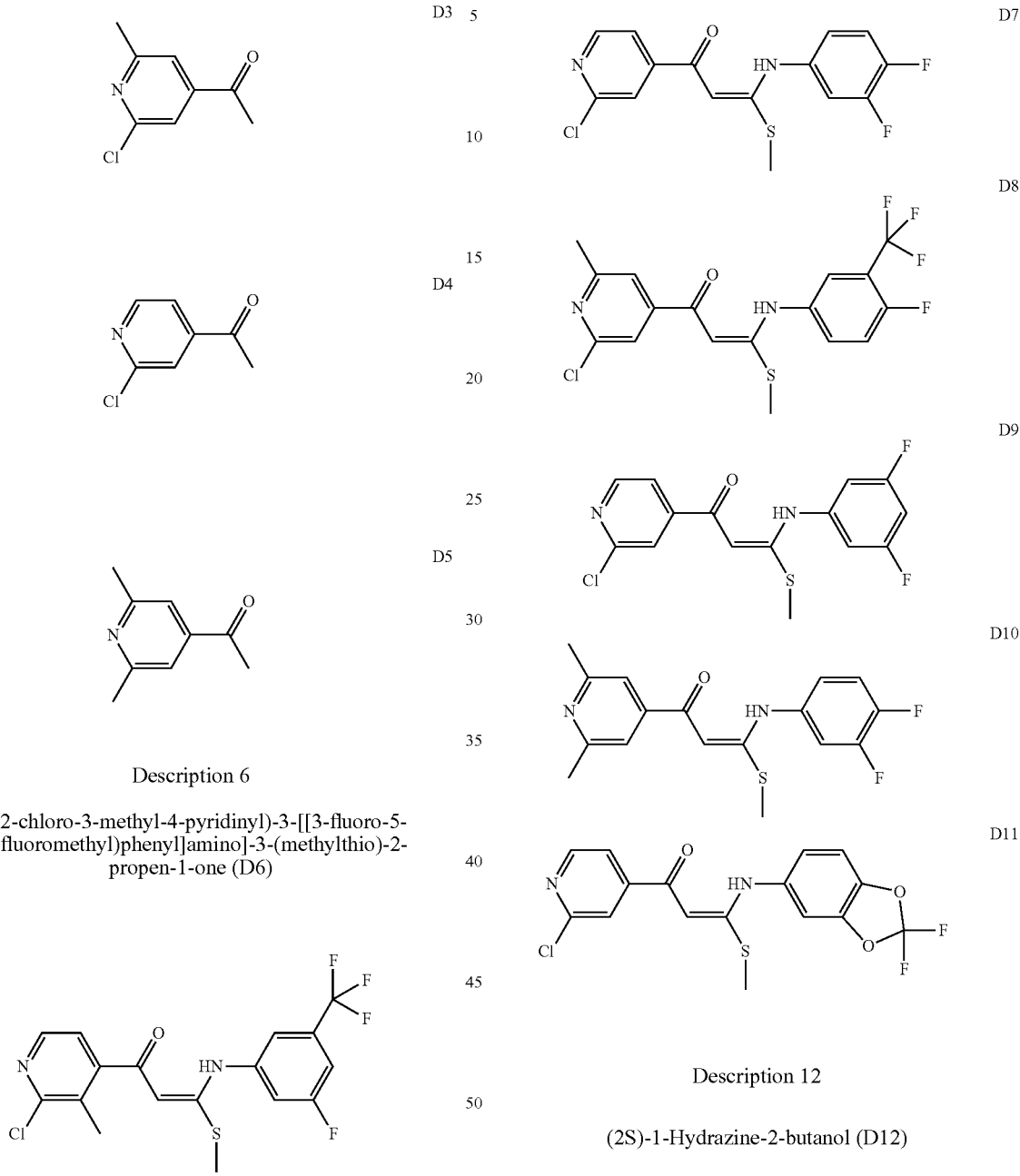

Description 6

1-(2-chloro-3-methyl-4-pyridinyl)-3-[[3-fluoro-5-(trifluoromethyl)phenyl]amino]-3-(methylthio)-2-propen-1-one (D6)

To a solution of D2 (5.8 g; 34.2 mmol) was dissolved in DMF (40 ml) at 0° C. was added NaH (60%) (1.64 g; 41 mmol) portionwise. A solution of D19 (prepared according to Description D17 and D18) (7.6 g; 34.2 mmol) in DMF (20 ml) was then added dropwise. The reaction mixture was stirred at room temperature for 30 min. CH$_3$I (4.85 g; 41 mmol) was added slowly and the reaction mixture was stirred at room temperature for 1 h. The solution was poured out into cold water (0-5° C.) and extracted with CH$_2$Cl$_2$. The organic layer was dried over MgSO$_4$, filtered and evaporated (coevaporated with 2×50 ml toluene). The residue was crystallized from Et$_2$O. The precipitate was filtered off and dried. Yield 8.28 g of D6 (LCMS showed 100% pure product).

Description 12

(2S)-1-Hydrazine-2-butanol (D12)

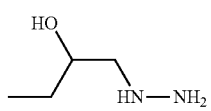

(2S)-2-ethyloxirane (24.5 g; 421.8 mmol) was dissolved in hydrazine.monohydrate (1:1) (84.5 g; 1687.3 mmol). The reaction mixture was then stirred for 2 h. at 50° C. The reaction mixture was then evaporated in a water bath at 50° C., Xylene added (×2) to co-evaporate the excess hydrazine.monohydrate (1:1). After cooling to room temperature, a white solid was obtained. Yield: 39.3 g of D12 (89.45%)

The following intermediate was also prepared by a procedure similar to that described in D12:

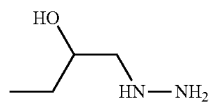

D13

Description 14-16 a) 2,3-dihydro-beta-oxo-1,4-benzodioxin-6-propane (dithioic) acid (D14)

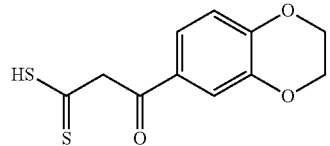 [SMILES: O=C(CC(=S)S)c1ccc2c(c1)OCCO2]

A suspension of NaH (60%) (8.69 g, 0.224 mol) in DMF (100 ml) was cooled to 0° C. To this suspension was slowly added 1-(2,3-dihydro-1,4-benzodioxin-6-yl)ethanone (20 g, 0.112 mol). The mixture was heated to room temperature and stirred for 2 h. The mixture was then cooled again to 0° C. and CS$_2$ (8.52 g, 0.112 mol) was slowly added. The reaction mixture was stirred for a further 2 h. before being used in the next reaction step without further purification.

b) 1-(2,3-dihydro-1,4-benzodioxin-6-yl)-3,3-bis(methylthio)-2-propen-1-one (D15)

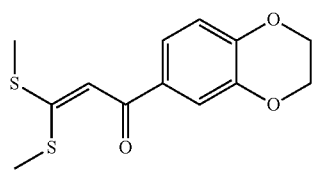 [SMILES: CSC(=CC(=O)c1ccc2c(c1)OCCO2)SC]

The reaction mixture from the previous reaction step, D14, (28.48 g, 0.112 mol) and DMF (100 ml)) was re-cooled to 0° C. and then CH$_3$I (32 g, 0.224 mol) was added slowly. The mixture was then warmed to room temperature and stirred for 30 min. After this period, the reaction mixture was poured over ice and the aqueous phase was extracted with ethyl acetate. The organic layer was dried (Na$_2$SO$_4$), filtered and the solvent was evaporated in vacuo. The crude product was purified by column chromatography over silica gel (eluent: petroleum ether/ethyl acetate 10/1). The desired fractions were collected and the solvent was evaporated in vacuo. Yield: 25 g of D15 (79.3%).

c) (2Z)-3-[(3,4-difluorophenyl)amino]-1-(2,3-dihydro-1,4-benzodioxin-6-yl)-3-(methylthio)-2-propen-1-one (D16)

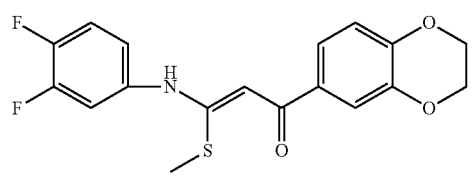 [SMILES: CS/C(=C\C(=O)c1ccc2c(c1)OCCO2)Nc1ccc(F)c(F)c1]

A solution of D15 (3 g, 0.0106 mol), 3,4-difluorobenzenamine (2.05 g, 0.0159 mol) and borontrifluoride-diethylether complex (0.17 g, 0.0106 mol) in dry toluene (100 ml) was refluxed for 2 h. The reaction mixture was then cooled and washed with hydrochloric acid (10%) and water. The crude product was purified by flash chromatography (eluent: petroleum ether/ethylacetate from 5/1 to 1/1). The desired fractions were collected and the solvent was evaporated in vacuo. Yield: 2.2 g of D16 (yield 57%).

Description 17-18 a) 3,4-Difluoro-5-methoxybenzenamine (D17)

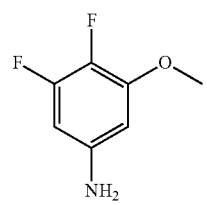

A mixture of 3,4,5-trifluorobenzenamine (40 g; 272 mmol) in NaOMe (30% in MeOH) (250 ml) was heated at reflux for 16 h. The reaction mixture was then poured onto ice with 37% aqueous HCl (150 ml)( ). CH$_2$Cl$_2$ was added and the pH of the reaction mixture was adjusted to pH=7-8 using an aqueous solution of Na$_2$CO$_3$. The organic layer was separated, dried (MgSO$_4$), filtered and the solvent was evaporated in vacuo. The residue was purified by column chromatography over silica gel (eluent: 50:50 heptane/CH$_2$Cl$_2$ to pure CH$_2$Cl$_2$). The pure fractions were collected and the solvent evaporated in vacuo.

Yield: 21.3 g of D17.

b) 1,2-Difluoro-5-isothiocyanato-3-methoxy-benzene (D18)

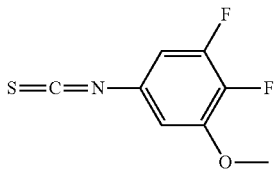

D17 (2.2 g; 12.3 mmol) was dissolved in CH$_2$Cl$_2$ (60 ml) in a 250-ml flask. 1,1'-carbonothioylbis-2(1H)-pyridinone (3.42 g; 14.7 mmol) was added and the reaction mixture was stirred at room temperature for 16 h. The reaction mixture was washed (×2) with water and with a 10% aqueous solution of Na$_2$CO$_3$. The organic layer was separated, dried (MgSO$_4$), filtered and the solvent evaporated in vacuo. The residue was purified by column chromatography over silica gel (eluent: heptane:CH$_2$Cl$_2$ from 70:30 to 50:50). The product fractions were collected and the solvent evaporated in vacuo. Yield: 2.02 g of D18 (82%).

The following intermediate was also prepared by a procedure similar to that described in D17 and D18:

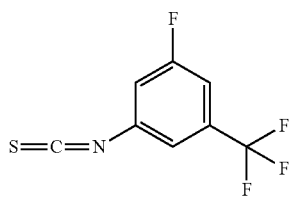

D19

Description 20

2-[[(3,4-difluoro-5-methoxyphenyl)amino]thioxomethyl]-1-[3-(dimethylamino)-3-oxopropyl]-hydrazinecarboxylic acid 1,1-dimethylethyl ester (D20)

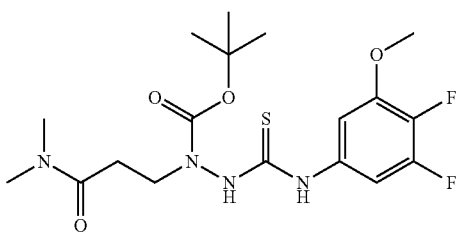 [SMILES: COc1cc(NC(=S)NN(CCC(=O)N(C)C)C(=O)OC(C)(C)C)cc(F)c1F]

DMAA (2 g; 20.2 mmol) was dissolved in EtOH (100 ml) in a 250 ml flask. Hydrazine.monohydrate (64%) (1:1) (2.4 g; 30.3 mmol) was added and the reaction mixture was stirred at room temperature for 2 h. The solvent was evaporated and the residue was co-evaporated with xylene (2×100 ml). The residue was dissolved in EtOH (50 ml) and cooled to 0° C. and Boc$_2$O (in EtOH solution) was added dropwise. Then the reaction mixture was warmed to room temperature slowly and stirred for a further 2 h. D18 (2.02 g; 10 mmol) was added to the reaction mixture, stirred overnight and then the solvent was evaporated in vacuo. The residue was purified by flash column chromatography over silica gel (Biotage flash purification system; gradient EtOAc/heptane from 30/70 to 70/30). The product fractions were collected and the solvent was evaporated in vacuo. Yield: 5.89 g of D20.

Description 21-23 a) 5-(2-chloro-6-methyl-4-pyridinyl)-N-[4-fluoro-3-(trifluoromethyl)phenyl]-1H-pyrazol-3-amine (D21)

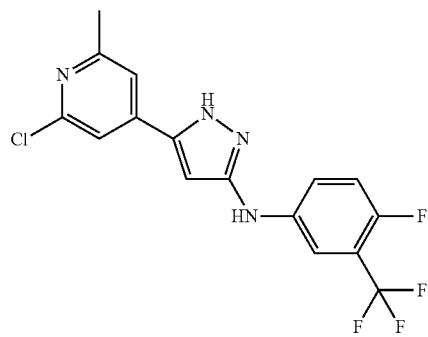 [SMILES: Cc1cc(-c2cc(Nc3ccc(F)c(C(F)(F)F)c3)n[nH]2)cc(Cl)n1]

D8 (1.45 g; 3.58 mmol) was added to a mixture of hydrazine.monohydrate (1:1) 64% (0.24 g; 4.66 mmol) in t-BuOH (40 ml) and the reaction mixture stirred for 2 h under reflux. The solvent was evaporated in vacuo, H$_2$O (10 ml) was added to the residue and then the mixture extracted with Et$_2$O.

The organic layer was dried (MgSO$_4$), filtered and the solvent evaporated in vacuo. Yield: 1.61 g of D21.

The following intermediate was also prepared by a procedure similar to that described in D21:

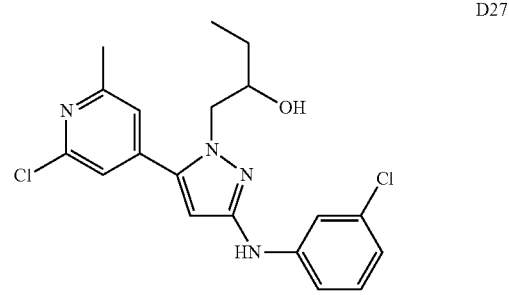 [SMILES: CCC(O)Cn1nc(Nc2cccc(Cl)c2)cc1-c1cc(C)nc(Cl)c1]

D27 b) [5-(2-chloro-6-methyl-4-pyridinyl)-1H-pyrazol-3-yl][4-fluoro-3-(trifluoromethyl)phenyl]-carbamic acid 1,1-dimethylethyl ester (D22)

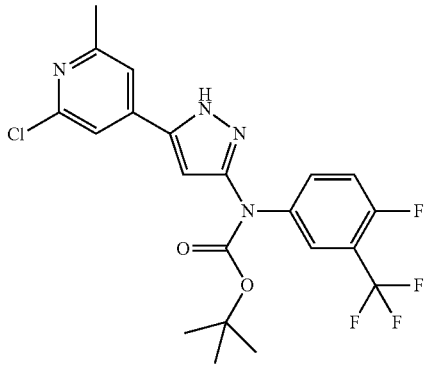 [SMILES: Cc1cc(-c2cc(N(C(=O)OC(C)(C)C)c3ccc(F)c(C(F)(F)F)c3)n[nH]2)cc(Cl)n1]

To a solution of D21 (1.65 g; 4.46 mmol) in DMF (20 ml), cooled to 0° C., was carefully added NaH (60% pure) (0.21 g; 5.35 mmol). The reaction mixture was stirred for 15 min., then Boc₂O (1.16 g; 5.35 mmol) was added. The ice bath was removed and the reaction mixture was allowed to warm to room temperature. The reaction mixture was then stirred for 16 h., quenched by addition of water, then extracted with EtOAc (3×30 ml). The combined organic phases were washed with brine, dried (MgSO₄), filtered and the solvent evaporated in vacuo. The residue was purified by column chromatography over silica gel (Biotage flash purification system; gradient CH₂Cl₂/10% in MeOH in CH₂Cl₂ from 100/0 to 0/100). Yield: 0.49 g of D22.

c) [5-(2-chloro-6-methyl-4-pyridinyl)-1-[(3S)-3-hydroxybutyl]-1H-pyrazol-3-yl][4-fluoro-3-(trifluoromethyl)phenyl]-carbamic acid 1,1-dimethylethyl ester (D23)

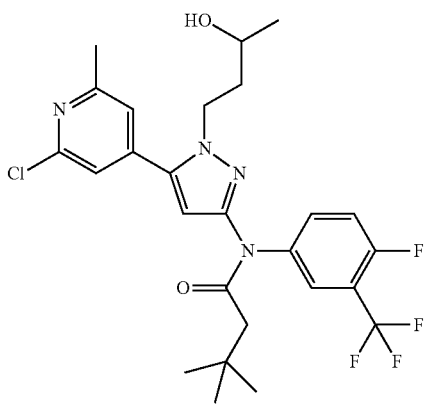 [SMILES: Cc1cc(-c2cc(N(C(=O)CC(C)(C)C)c3ccc(F)c(C(F)(F)F)c3)nn2CCC(C)O)cc(Cl)n1]

D22 (0.39 g; 0.83 mmol) and Cs₂CO₃ (0.5 g) were dissolved in DMF (20 ml) and then 1-(4-methylbenzenesulfonate)-1,3-butanediol (0.3 g; 1.23 mmol) was added carefully. The reaction mixture was stirred for 16 h. at room temperature, before being quenched with water and extracted with CH₂Cl₂ (2×20 ml). The combined organic phases were washed with brine, dried (MgSO₄), filtered and the solvent was evaporated in vacuo.

The residue was purified by flash chromatography (gradient CH₂Cl₂/10% MeOH in CH₂Cl₂ from 100/0 to 0/100). Yield: 0.5 g of D23.

Description 24-26 a) 4-[3-[(3,4-difluorophenyl)amino]-1-[(2S)-2-[[(1,1-dimethylethyl)dimethylsilyl]oxy]butyl]-1H-pyrazol-5-yl]-2-pyridine carboxylic acid methyl ester (D24)

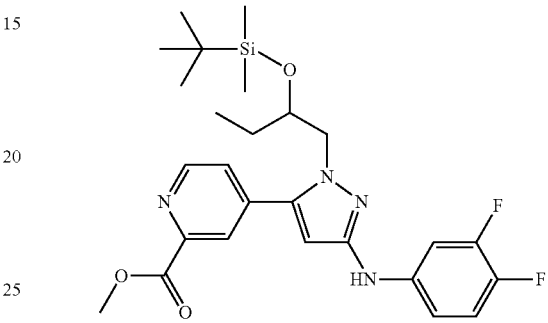

Chloro(1,1-dimethylethyl)dimethylsilane (0.0701 g; 0.465 mmol) and 4H-imidazole (0.0528 g; 0.775 mmol) were dissolved in dry DMF (15 ml) and then E5 (0.156 g; 0.388 mmol) was added. The reaction mixture was stirred at 80° C. for 4 h., cooled to room temperature, poured onto H₂O and then extracted with Et₂O. The organic layer was dried (MgSO₄), filtered and the solvent was evaporated in vacuo. The residue was purified by flash column chromatography over silica gel (Biotage flash purification system; gradient acetone/heptane from 20/80 to 50/50). Yield: 190 mg of D24.

b) 4-[3-[(3,4-difluorophenyl)amino]-1-[(2S)-2-[[(1,1-dimethylethyl)dimethylsilyl]oxy]butyl]-1H-pyrazol-5-yl]-2-pyridinemethanol (D25)

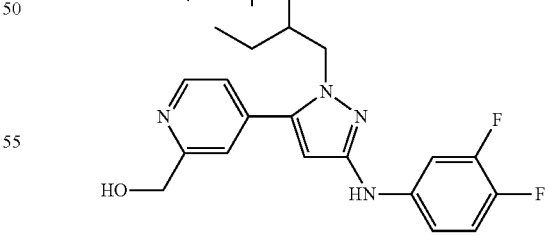

A mixture of D24 (0.187 g; 0.362 mmol) and NaBH₄ (0.2 g) in THF (5 ml) and MeOH (5 ml) were cooled to 0° C. then CaCl₂.2H₂O (0.2 g) was added.

The reaction mixture was warmed up to room temperature and stirred for 1 h. The mixture was then quenched with saturated NH₄Cl and extracted with EtOAc (×2). The organic layer was dried (MgSO₄), filtered and the solvent evaporated in vacuo. The residue was used in the next step without further purification.

c) N-(3,4-difluorophenyl)-1-[(2S)-2-[[(1,1-dimethyl-ethyl)dimethylsilyl]oxy]butyl]-5-[2-(methoxymethyl)-4-pyridinyl]-1H-pyrazol-3-amine (D26)

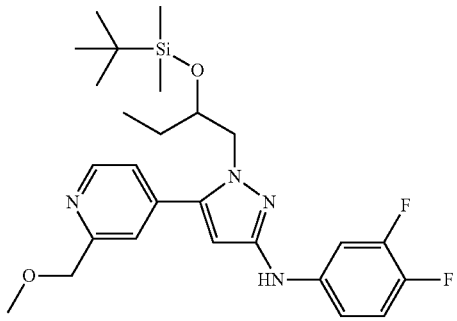 [SMILES: CCC(Cn1nc(Nc2ccc(F)c(F)c2)cc1-c1ccnc(COC)c1)O[Si](C)(C)C(C)(C)C]

To a suspension of D25 (0.15 g; 0.307 mmol) and Et₃N (0.1 ml) in THF at room temperature was added methanesulfonyl chloride (0.0238 ml; 0.307 mmol; 1.48 g/ml). After 15 min. when the suspension had dissolved, NaOMe (30% in MeOH) (1.5 ml) was added dropwise and the reaction mixture was stirred at room temperature for 2 h. The mixture was quenched with water and extracted with EtOAc (×2). The organic layer was dried (MgSO₄), filtered and the solvent evaporated in vacuo. The residue, containing D26 was used for further reactions without purification.

B. Preparation of the Final Compounds

Example 1

5-(2-chloro-3-methyl-4-pyridinyl)-3-[[3-fluoro-5-(trifluoromethyl)phenyl]amino]-N,N-dimethyl-1H-pyrazole-1-propanamide (E1)

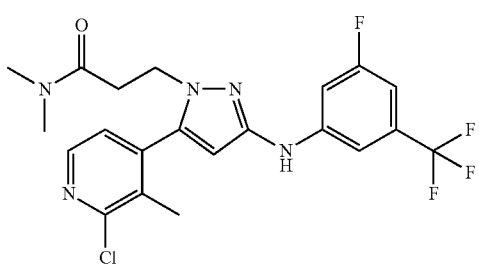 [SMILES: Cc1c(-c2cc(Nc3cc(F)cc(C(F)(F)F)c3)nn2CCC(=O)N(C)C)ccnc1Cl]

D6 (prepared according to Description 6) (1.0 g; 2.48 mmol) was added to a mixture of 3-hydrazinyl-N,N-dimethylpropanamide (0.65 g; 4.95 mmol) in t-BuOH (20 ml) and the reaction mixture stirred at 150° C. for 16 h. The solvent was then evaporated in vacuo and the residue purified by flash chromatography over silica gel (Biotage flash purification system: gradient acetone/heptane from 20/80 to 50/50). The solvent was then evaporated in vacuo and two fractions were collected. The desired fraction yielded 0.40 g of E1 (34.3%).

Example 2 a) 5-(2-chloro-4-pyridinyl)-3-[(2,2-difluoro-1,3-benzodioxol-5-yl)amino]-N,N-dimethyl-1H-pyrazole-1-propanamide (E2)

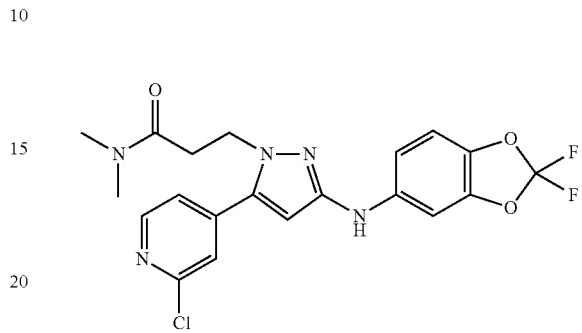

D11 (prepared according to Description 6) (0.98 g; 2.6 mmol) and 3-hydrazinyl-N,N-dimethylpropanamide (0.77 g; 5.9 mmol) were added to a mixture of ZnCl₂ (0.5 M in THF) (5.1 ml; 2.6 mmol) in THF (30 ml) and the reaction mixture stirred at 150° C. for 3 h. The solvent was evaporated in vacuo and the residue purified by flash column chromatography over silica gel (Biotage flash purification system; gradient acetone/heptane from 20/80 to 50/50). Two fractions were collected. The desired fraction yielded 0.30 g of E2 (2.5%).

b) 5-(2-chloro-4-pyridinyl)-3-[(2,2-difluoro-1,3-benzodioxol-5-yl)amino]-N,N-dimethyl-1H-pyrazole-1-propanamide (E2)

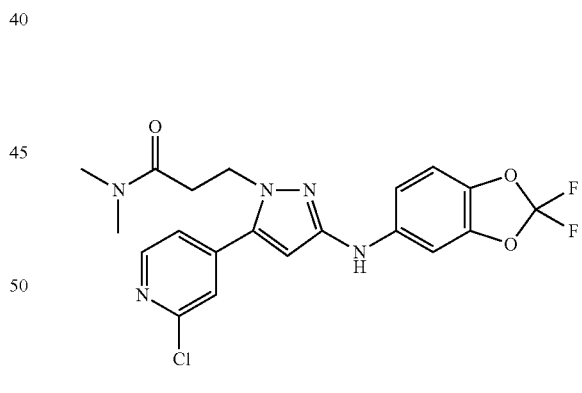

D11 (prepared according to Description 6) (0.85 g; 2.2 mmol) was added to a mixture of 3-hydrazinyl-N,N-dimethylpropanamide (0.50 g; 3.8 mmol) in t-BuOH (30 ml), then 1,1,1-trifluoromethanesulfonic acid, lanthanum (3+) salt (3:1) (0.105 g; 2 mmol) was added. The reaction mixture was stirred at reflux for 48 h and then the solvent was evaporated in vacuo. The residue was purified by flash column chromatography over silica gel (Biotage flash purification system; gradient acetone/heptane from 20/80 to 50/50) and 2 fractions were collected. The solvent was evaporated in vacuo. The desired fraction yielded 0.20 g of E2 (2%).

Example 3

5-(2-chloro-4-pyridinyl)-3-[(3,4-difluorophenyl)amino]-N,N-dimethyl-1H-pyrazole-1-propanamide (E3)

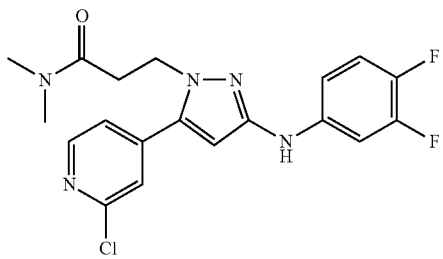 [SMILES: CN(C)C(=O)CCn1nc(Nc2ccc(F)c(F)c2)cc1-c1ccnc(Cl)c1]

D7 (prepared according to Description D6) (0.71 g; 0.0021 mol) was dissolved in t-BuOH (50 ml), then 3-hydrazinyl-N,N-dimethylpropanamide (0.71 g; 0.0055 mol) was added. The reaction mixture was stirred and refluxed overnight, then the solvent was evaporated in vacuo. The product was purified by reversed-phase high-performance liquid chromatography (Shandon Hyperprep® C18 BDS (Base Deactivated Silica) 8 μm, 250 g, I.D. 5 cm). A gradient with 3 mobile phases was applied. Phase A: a 0.25% NH$_4$HCO$_3$ solution in water; phase B: CH$_3$OH; phase C: CH$_3$CN). Two fractions were collected. The desired fraction yielded: 0.14 g of E3 (16.5%).

Example 4

(alphaS)-5-(2-chloro-6-methyl-4-pyridinyl)-3-[[4-fluoro-3-(trifluoromethyl)phenyl]amino]-alpha-methyl-1H-pyrazole-1-propanol (E4)

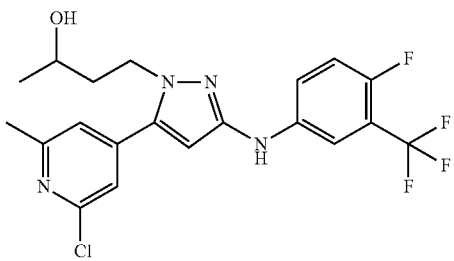 [SMILES: Cc1cc(-c2cc(Nc3ccc(F)c(C(F)(F)F)c3)nn2CCC(C)O)cc(Cl)n1]

D23 (prepared according to Description D23) (0.5 g; 0.92 mmol) was dissolved in CH$_2$Cl$_2$ (20 ml) and then TFA was added (1.4 ml; 18.4 mmol). The reaction mixture was stirred at room temperature for 2 h. The reaction was quenched with a saturated solution of NaHCO$_3$, then extracted with CH$_2$Cl$_2$ (3×30 ml). The combined organic phases were washed with brine, dried (MgSO$_4$), filtered and the solvent was evaporated in vacuo. The residue was purified by flash chromatography over silica gel (Biotage flash purification system; gradient CH$_2$Cl$_2$/10% MeOH in CH$_2$Cl$_2$ from 100/0 to 0/100). Yield: 0.26 g of E4 (63.81%).

Example 5

4-[3-[(3,4-difluorophenyl)amino]-1-[(2S)-2-hydroxybutyl]-1H-pyrazol-5-yl]-2-pyridinecarboxylic acid methyl ester (E5)

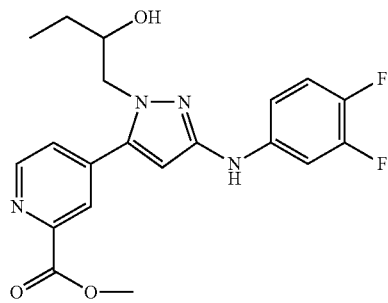 [SMILES: CCC(O)Cn1nc(Nc2ccc(F)c(F)c2)cc1-c1ccnc(C(=O)OC)c1]

A 75-ml stainless steel autoclave was charged under a N$_2$ atmosphere with E48 (prepared according to Example 1) (2 g; 5.28 mmol), Pd(OAc)$_2$ (0.0236 g; 0.106 mmol), 1.3 bis (diphenylphosphino)propane (0.087 g; 0.211 mmol), potassium acetate (1; 55 g; 15.8 mmol) and methanol/THF (1:1) (40 ml). The autoclave was closed and pressurized to 50 bar with CO and the reaction was carried out for 16 h at a temperature of 125° C. The residue was purified by flash column chromatography over silica gel (Biotage flash purification system; gradient acetone/heptane from 20/80 to 70/30) and 2 fractions were obtained. The desired fraction yielded 267 mg of E5 (13%).

Example 6

(alphaS)-3-[(3,4-difluorophenyl)amino]-alpha-ethyl-5-[2-(methoxymethyl)-4-pyridinyl]-1H-pyrazole-1-ethanol (E6)

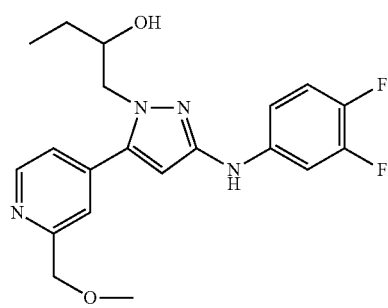 [SMILES: CCC(O)Cn1nc(Nc2ccc(F)c(F)c2)cc1-c1ccnc(COC)c1]

D26 (prepared according to Description D26) (0.15 g; 0.298 mmol) was dissolved in TBAF (10 ml) and the reaction mixture was stirred at room temperature for 2 h. The solvent was then evaporated in vacuo and the residue dissolved in CH$_2$Cl$_2$ and washed several times with H$_2$O. The organic layer was separated and dried (MgSO$_4$) The filtrate left on oil was filtered and the solvent evaporated in vacuo. The product was purified by reversed-phase high-performance liquid chromatography (Shandon Hyperprep® C$_{18}$ BDS (Base Deactivated Silica) 8 μm, 250 g, I.D. 5 cm). A gradient with 3 mobile phases was applied. Phase A: a 0.25% NH$_4$HCO$_3$ solution in water; phase B (optional): MeOH; phase C: CH$_3$CN). The fractions were collected and worked-up. The desired fraction yielded 34.5 mg of E6 (29.8%).

Example 7

3-[(3,4-difluorophenyl)amino]-5-(2,3-dihydro-1,4-benzodioxin-6-yl)-N-methyl-1H-pyrazole-1-acetamide (E7)

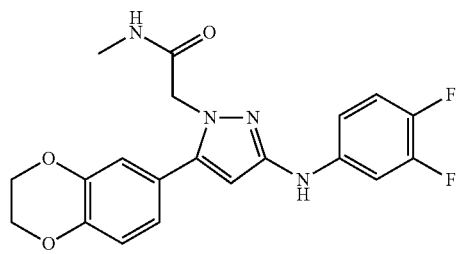 [SMILES: CNC(=O)Cn1nc(Nc2ccc(F)c(F)c2)cc1-c1ccc2c(c1)OCCO2]

A mixture of E10 (prepared according to Description E10) (0.55 g; 1.324 mmol) and MeNH$_2$/EtOH (15 ml; 1.324 mmol) was heated overnight in a sealed vessel at 90° C. The mixture was concentrated and the residue was purified by preparative HPLC (eluent: 0.1% TFA in CH$_3$CN/0.1% TFA in H$_2$O). The product fractions were collected and neutralized with a saturated NaHCO$_3$ solution. The desired product was extracted with EtOAc (2×100 ml). The separated organic layer was dried (Na$_2$SO$_4$), filtered and the solvent evaporated in vacuo. Yield: 0.230 g of E7 (43.6%).

Example 8

(alphaS)-3-[(3,5-difluorophenyl)amino]-alpha-ethyl-5-[2-(ethylamino)-4-pyridinyl]-1H-pyrazole-1-ethanol (E8)

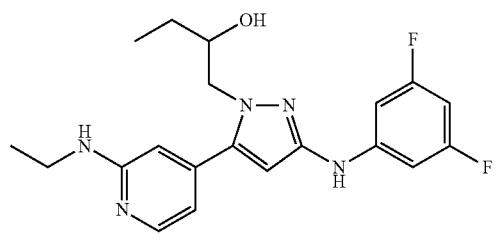 [SMILES: CCNc1cc(-c2cc(Nc3cc(F)cc(F)c3)nn2CC(O)CC)ccn1]

E47 (prepared according to Example 1) (0.47 g; 1.24 mmol) was dissolved in MeOH (20 ml) and then EtNH$_2$ (2 g) was added. The reaction mixture was stirred at 160° C. under pressure for 24 h and the solvent was evaporated in vacuo.

The residue was purified by reversed-phase high-performance liquid chromatography (Shandon Hyperprep® C$_{18}$ BDS (Base Deactivated Silica) 8 μm, 250 g, I.D. 5 cm). A gradient with 3 mobile phases was applied. Phase A: a 0.25% NH$_4$HCO$_3$ solution in water; phase B (optional): MeOH; phase C: CH$_3$CN). The fractions were collected and purified again by reversed phase high-performance liquid chromatography (Shandon Hyperprep® C$_{18}$ BDS (Base Deactivated Silica) 8 μm, 250 g, I.D. 5 cm). A gradient with 2 mobile phases was applied. Phase A: 90% of a 0.5% NH$_4$OAc solution in water+10% CH$_3$CN; phase B: CH$_3$CN). The fractions were collected and worked-up. The desired fraction yielded 0.0789 g of E8 (16%).

Example 9

3-[[3-fluoro-5-(trifluoromethyl)phenyl]amino]-N,N-dimethyl-5-(3-methyl-4-pyridinyl)-1H-pyrazole-1-propanamide (E9)

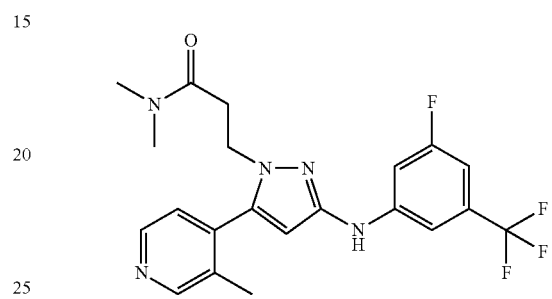

E1 (0.40 g; 0.85 mmol) was dissolved in THF (50 ml) and then Et$_3$N (0.5 ml), 10%, RaNi (0.1 g) and thiophene solution (0.1 ml) were added. The reaction mixture was stirred under H$_2$ pressure overnight. The solvent was evaporated in vacuo and then H$_2$O (10 ml) was added. The water phase was extracted by EtOAc (3×30 ml), the combined organic layers were washed by brine, dried (MgSO$_4$), filtered and the solvent was evaporated in vacuo. The residue was purified by reversed-phase high-performance liquid chromatography (Shandon Hyperprep® C$_{18}$ BDS (Base Deactivated Silica) 8 μm, 250 g, I.D. 5 cm). A gradient with 2 mobile phases was applied. Phase A: a 0.25% NH$_4$HCO$_3$ solution in water; phase B: CH$_3$CN). The fractions were collected and worked-up. The desired fraction yielded 0.25 g of E9 (67.55%).

Example 10

3-[(3,4-difluorophenyl)amino]-5-(2,3-dihydro-1,4-benzodioxin-6-yl)-1H-pyrazole-1-acetic acid ethyl ester (E10)

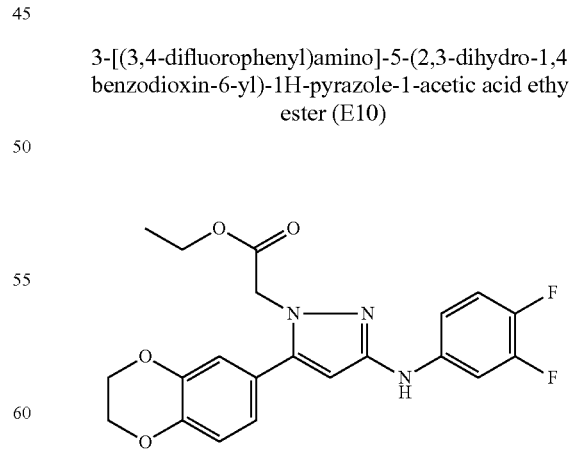

A mixture of D16 (0.00138 mol), 2-hydrazinyl-acetic acid ethyl ester.monohydrochloride (1:1) (0.00276 mol) and K$_2$CO$_3$ (0.00206 mol) in t-BuOH (100 ml) was stirred at 85° C. overnight in a sealed reaction vessel. The reaction mixture was cooled, filtered and the filtrate's solvent evaporated in vacuo. Yield: 0.55 g of E10 (96.5%).

Example 185

(alphaS)-3-[(3-chlorophenyl)amino]-alpha-ethyl-5-[2-methyl-4-pyridinyl]-1H-pyrazole-1-ethanol (E185)

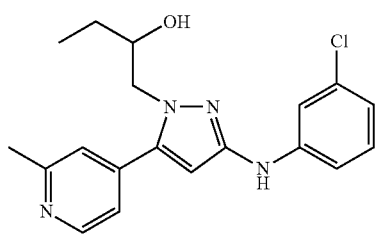 [SMILES: CCC(O)Cn1nc(Nc2cccc(Cl)c2)cc1-c1ccnc(C)c1]

D27 (420 mg; 1.073 mmol), [1,3-bis[2,6-bis(1-methylethyl)phenyl]-2-imidazolidinylidene]chloro(η3-2-propenyl)palladium (CAS [478980-01-7]; catalyst) (61.68 mg; 0.107 mmol), NaOMe 0.5M in CH$_3$OH (0.6 ml) and i-PrOH (4 ml) were stirred in the microwave during 10 minutes at 60° C. The reaction mixture was evaporated, washed with water and extracted with CH$_2$Cl$_2$. The organic layer was dried on MgSO$_4$, filtered and evaporated. The residue was purified by high-performance liquid chromatography. Yield: 30.9 mg of E185 (8.07%).

The following compounds of formula (I), as depicted in Tables 1 and 2, were prepared by analogy to the above examples (Ex. No.'s).

TABLE 1

| Co. No. | Ex. No. | Z | L | R$^x$ |
|---|---|---|---|---|
| 103 | Ex. 9 | H$_3$C-N(CH$_3$)-C(=O)-CH$_2$-CH$_2$- | 3-methoxyphenyl | 3-F, 4-F |
| 11 | Ex. 1 | H$_3$C-N(CH$_3$)-C(=O)-CH$_2$-CH$_2$- | 2-chloro-3-methoxyphenyl | 3-F, 4-F |
| 12 | Ex. 1 | H$_3$C-N(CH$_3$)-C(=O)-CH$_2$-CH$_2$- | 3-chloro-4-methoxyphenyl | 3-F, 4-F |
| 13 | Ex. 9 | H$_3$C-NH-C(=O)-CH$_2$- | pyridin-3-yl | 3-CF$_3$ |
| 14 | Ex. 9 | H$_3$C-NH-C(=O)-CH$_2$- | pyridin-3-yl | 3-OCF$_3$ |

TABLE 1-continued
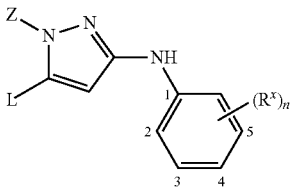
| Co. No. | Ex. No. | Z | L | Rˣ |
|---|---|---|---|---|
| 15 | Ex. 9 | 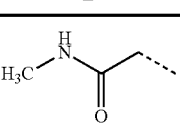 | 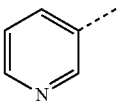 | 3-F, 4-F, 5-F |
| 16 | Ex. 9 | 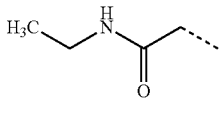 | 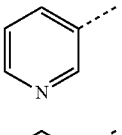 | 3-F, 4-F |
| 17 | Ex. 9 | 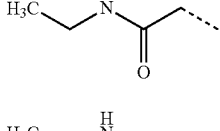 | 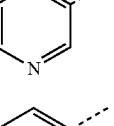 | 3-OCF₃ |
| 18 | Ex. 9 | 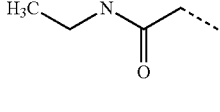 | 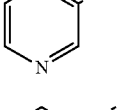 | 3-CF₃ |
| 19 | Ex. 9 | 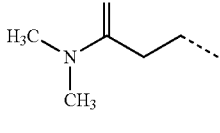 | 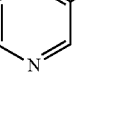 | 3-F, 4-F |
| 20 | Ex. 9 | 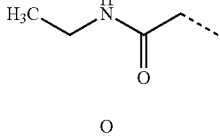 | 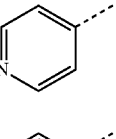 | 3-F, 4-F |
| 21 | Ex. 9 | 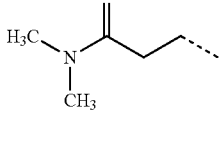 | 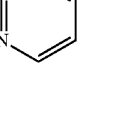 | 3-F, 4-F |
| 22 | Ex. 2 | 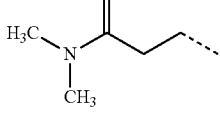 | 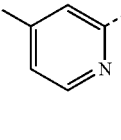 | 3-F, 4-F |
| 23 | Ex. 1 | 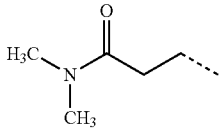 | 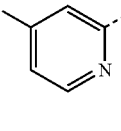 | 3-CF₃, 4-F |
| 24 | Ex. 2 | 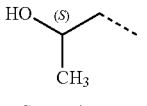<br>S-enantiomer | 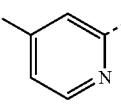 | 3-F, 4-F |

TABLE 1-continued

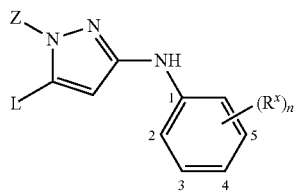

| Co. No. | Ex. No. | Z | L | R$^x$ |
|---|---|---|---|---|
| 25 | Ex. 1 | HO-CH(S)(CH$_3$)- (S-enantiomer) | 4-methyl-pyridin-2-yl | 3-CF$_3$, 4-F |
| 26 | Ex. 1 | (CH$_3$)$_2$N-C(O)-CH$_2$CH$_2$- | 4-methyl-pyridin-2-yl | 3-F, 5-F |
| 27 | Ex. 7 | CH$_3$CH$_2$-NH-C(O)-CH$_2$- | 6-methyl-pyridin-3-yl | 3-CF$_3$, 4-F |
| 28 | Ex. 2 | (CH$_3$)$_2$N-C(O)-CH$_2$CH$_2$- | 6-methyl-pyridin-3-yl | 3-CF$_3$, 4-F |
| 29 | Ex. 1 | HO-CH(S)(CH$_2$CH$_3$)- (S-enantiomer) | 6-methyl-pyridin-3-yl | 3-CF$_3$, 4-F |
| 30 | Ex. 9 | CH$_3$-NH-C(O)-CH$_2$- | 3-methyl-pyridin-4-yl | 3-CF$_3$, 5-F |
| 31 | Ex. 9 | CH$_3$CH$_2$-NH-C(O)-CH$_2$- | 3-methyl-pyridin-4-yl | 3-CF$_3$, 5-F |
| 9 | Ex. 9 | (CH$_3$)$_2$N-C(O)-CH$_2$CH$_2$- | 3-methyl-pyridin-4-yl | 3-CF$_3$, 5-F |
| 32 | Ex. 7 | CH$_3$-NH-C(O)-CH$_2$- | 2-methyl-pyridin-4-yl | 3-CF$_3$ |

TABLE 1-continued
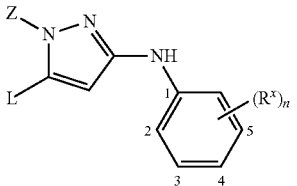
| Co. No. | Ex. No. | Z | L | R$^x$ |
|---|---|---|---|---|
| 35 | Ex. 7 | 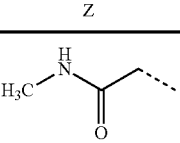 | 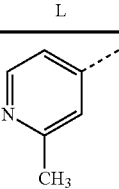 | 3-OCF$_3$ |
| 34 | Ex. 9 | 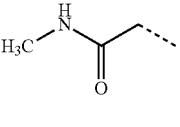 | 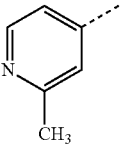 | 3-CF$_3$, 4-F |
| 33 | Ex. 7 | 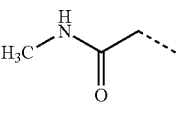 | 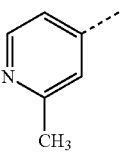 | 3-Cl, 5-F |
| 107 | Ex. 7 | 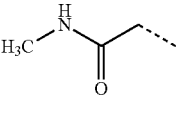 | 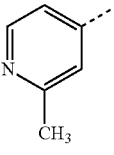 | 2-F, 3-F, 4-F |
| 109 | Ex. 7 | 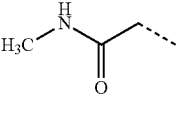 | 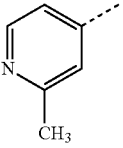 | 3-F, 4-F, 5-F |
| 36 | Ex. 7 | 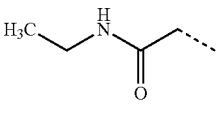 | 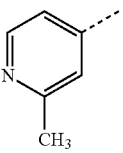 | 3-CF$_3$ |
| 37 | Ex. 7 | 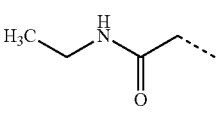 | 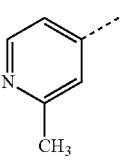 | 3-OCF$_3$ |
| 111 | Ex. 9 | 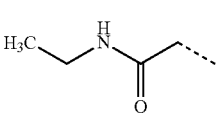 | 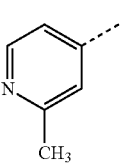 | 3-Cl |

TABLE 1-continued
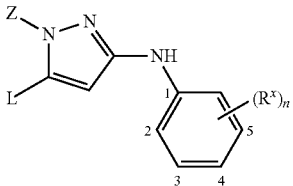
| Co. No. | Ex. No. | Z | L | R$^x$ |
|---|---|---|---|---|
| 137 | Ex. 9 | 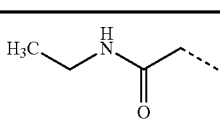 | 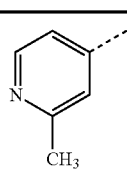 | 2-F, 3-Cl |
| 38 | Ex. 9 | 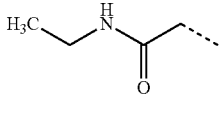 | 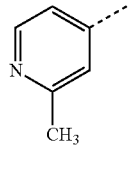 | 3-CF$_3$, 4-F |
| 39 | Ex. 7 | 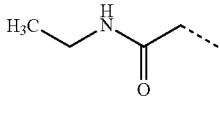 | 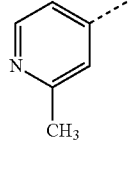 | 3-Cl, 5-F |
| 108 | Ex. 7 | 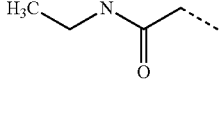 | 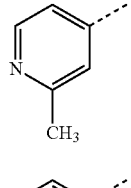 | 3-Cl, 5-OCH$_3$ |
| 181 | Ex. 9 | 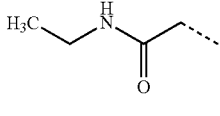 | 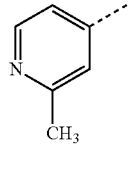 | 3-CF$_3$, 5-OCH$_3$ |
| 125 | Ex. 7 | 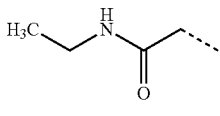 | 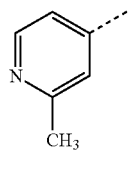 | 2-F, 3-F, 4-F |
| 128 | Ex. 7 | 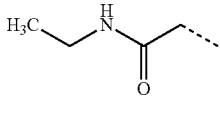 | 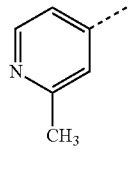 | 3-F, 4-F, 5-F |
| 176 | Ex. 9 | 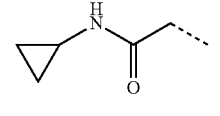 | 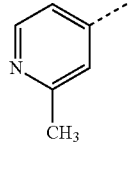 | 2-F |

TABLE 1-continued
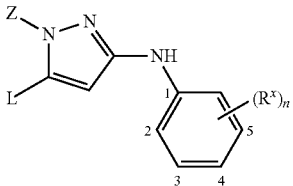
| Co. No. | Ex. No. | Z | L | R$^x$ |
|---|---|---|---|---|
| 123 | Ex. 9 | 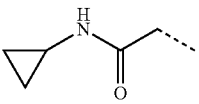 | 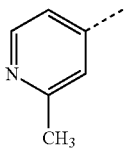 | 3-Cl |
| 110 | Ex. 7 | 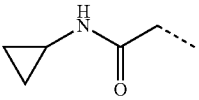 | 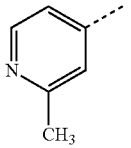 | 3-Cl, 5-OCH$_3$ |
| 104 | Ex. 9 | 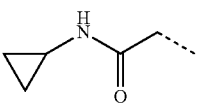 | 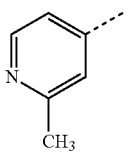 | 3-CF$_3$, 5-OCH$_3$ |
| 116 | Ex. 7 | 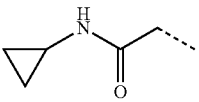 | 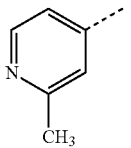 | 2-F, 3-F, 4-F |
| 163 | Ex. 9 | 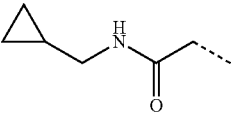 | 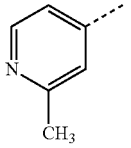 | 3-Cl |
| 170 | Ex. 9 | 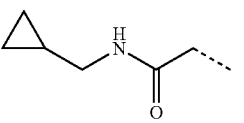 | 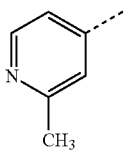 | 2-F, 3-Cl |
| 132 | Ex. 7 | 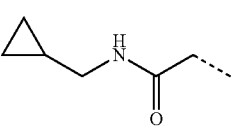 | 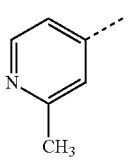 | 3-Cl, 5-OCH$_3$ |
| 131 | Ex. 9 | 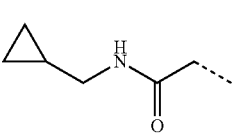 | 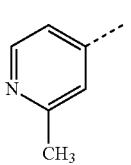 | 3-CF$_3$, 5-OCH$_3$ |

TABLE 1-continued

| Co. No. | Ex. No. | Z | L | R^x |
|---|---|---|---|---|
| 164 | Ex. 7 | cyclopropylmethyl-NH-C(O)-CH2- | 2-methylpyridin-4-yl | 2-F, 3-F, 4-F |
| 168 | Ex. 7 | cyclopropylmethyl-NH-C(O)-CH2- | 2-methylpyridin-4-yl | 3-F, 4-F, 5-F |
| 146 | Ex. 9 | (CH3)2N-C(O)-CH2CH2- | 2-methylpyridin-4-yl | 3-Cl |
| 124 | Ex. 9 | (CH3)2N-C(O)-CH2CH2- | 2-methylpyridin-4-yl | 2-F, 3-Cl |
| 40 | Ex. 9 | (CH3)2N-C(O)-CH2CH2- | 2-methylpyridin-4-yl | 3-F, 4-F |
| 41 | Ex. 1 | (CH3)2N-C(O)-CH2CH2- | 2-methylpyridin-4-yl | 3-Cl, 5-F |
| 126 | Ex. 1 | (CH3)2N-C(O)-CH2CH2- | 2-methylpyridin-4-yl | 3-Cl, 5-OCH3 |
| 143 | Ex. 9 | (CH3)2N-C(O)-CH2CH2- | 2-methylpyridin-4-yl | 3-CF3, 5-OCH3 |

TABLE 1-continued

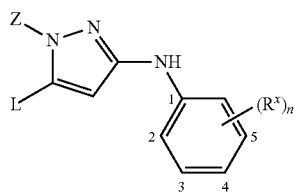

| Co. No. | Ex. No. | Z | L | R^x |
|---|---|---|---|---|
| 166 | Ex. 1 | H3C-N(CH3)-C(=O)-CH2CH2- | 2-methylpyridin-4-yl | 2-F, 3-F, 4-F |
| 142 | Ex. 1 | H3C-N(CH3)-C(=O)-CH2CH2- | 2-methylpyridin-4-yl | 3-F, 4-F, 5-F |
| 42 | Ex. 1 | HO-CH(CH3)-CH2- (S-enantiomer) | 2-methylpyridin-4-yl | 3-Cl, 5-F |
| 43 | Ex. 9 | HO-CH(CH3)-CH2- (S-enantiomer) | 2-methylpyridin-4-yl | 3-CF3, 4-F |
| 44 | Ex. 1 | HO-CH(CH3)-CH2- (S-enantiomer) | 2-methylpyridin-4-yl | 3-F, 4-F, 5-F |
| 185 | Ex. 185 | HO-CH(CH2CH3)-CH2- (S-enantiomer) | 2-methylpyridin-4-yl | 3-Cl |
| 118 | Ex. 9 | HO-CH(CH2CH3)-CH2- (S-enantiomer) | 2-methylpyridin-4-yl | 2-F, 3-Cl |
| 45 | Ex. 9 | HO-CH(CH2CH3)-CH2- (S-enantiomer) | 2-methylpyridin-4-yl | 3-F, 4-F |

TABLE 1-continued

| Co. No. | Ex. No. | Z | L | R$^x$ |
|---|---|---|---|---|
| 46 | Ex. 9 | HO-CH(S)(CH₂-)(CH₂CH₃), S-enantiomer | 2-methyl-pyridin-4-yl | 3-CF₃, 4-F |
| 122 | Ex. 1 | HO-CH(S)(CH₂-)(CH₂CH₃), S-enantiomer | 2-methyl-pyridin-4-yl | 3-Cl, 5-OCH₃ |
| 183 | Ex. 9 | HO-CH(S)(CH₂-)(CH₂CH₃), S-enantiomer | 2-methyl-pyridin-4-yl | 3-CF₃, 5-OCH₃ |
| 134 | Ex. 9 | HO-CH(S)(CH₃)(CH₂-), S-enantiomer | 2-methyl-pyridin-4-yl | 2-F, 3-F, 4-F |
| 106 | Ex. 7 | H₃C-NH-C(=O)-CH₂- | 2-(methoxymethyl)pyridin-4-yl | 2-F, 3-Cl |
| 184 | Ex. 1 | HO-CH(S)(CH₂-)(CH₂CH₃), S-enantiomer | 2-(methoxymethyl)pyridin-4-yl | 2-F, 3-Cl |
| 99 | Ex. 6 | HO-CH(S)(CH₂-)(CH₂CH₃), S-enantiomer | 2-(methoxymethyl)pyridin-4-yl | 3-CF₃, 5-OCH₃ |
| 3 | Ex. 3 | (H₃C)₂N-C(=O)-CH₂CH₂- | 2-chloro-pyridin-4-yl | 3-F, 4-F |

TABLE 1-continued

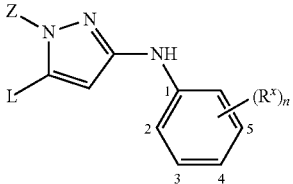

| Co. No. | Ex. No. | Z | L | R$^x$ |
|---|---|---|---|---|
| 47 | Ex. 1 | HO-CH(S)(CH₃)-CH₂- S-enantiomer | 2-Cl-pyridin-4-yl | 3-F, 5-F |
| 48 | Ex. 1 | HO-CH(S)(CH₃)-CH₂- S-enantiomer | 2-Cl-pyridin-4-yl | 3-F, 4-F |
| 49 | Ex. 9 | H₃C-CH(S)(OH)-CH₂- S-enantiomer | 2-CH₃-pyridin-4-yl | 3-CF₃, 4-F |
| 50 | Ex. 7 | H₃C-NH-C(O)-CH₂- | 2,3-di-CH₃-pyridin-4-yl | 3-CF₃, 5-OCH₃ |
| 51 | Ex. 7 | H₃C-CH₂-NH-C(O)-CH₂- | 2,3-di-CH₃-pyridin-4-yl | 3-CF₃, 5-OCH₃ |
| 52 | Ex. 1 | (H₃C)₂N-C(O)-CH₂-CH₂- | 2,3-di-CH₃-pyridin-4-yl | 3-CF₃, 5-OCH₃ |
| 53 | Ex. 1 | HO-CH(S)(CH₃)-CH₂- S-enantiomer | 2,3-di-CH₃-pyridin-4-yl | 3-CF₃, 5-OCH₃ |
| 1 | Ex. 1 | (H₃C)₂N-C(O)-CH₂-CH₂- | 2-Cl-3-CH₃-pyridin-4-yl | 3-F, 5-CF₃ |

TABLE 1-continued

| Co. No. | Ex. No. | Z | L | R$^x$ |
|---|---|---|---|---|
| 115 | Ex. 1 | HO—CH(S)(CH₂CH₃)— (S-enantiomer) | 3-Cl, 2-CH₃, 6-... pyridin-4-yl | 3-CF$_3$, 5-OCH$_3$ |
| 54 | Ex. 7 | H₃C-NH-C(O)-CH₂- | 2,6-di(CH₃)-pyridin-4-yl | 3-Cl |
| 117 | Ex. 7 | H₃C-NH-C(O)-CH₂- | 2,6-di(CH₃)-pyridin-4-yl | 3-CF$_3$ |
| 129 | Ex. 7 | H₃C-NH-C(O)-CH₂- | 2,6-di(CH₃)-pyridin-4-yl | 3-OCF$_3$ |
| 141 | Ex. 7 | H₃C-NH-C(O)-CH₂- | 2,6-di(CH₃)-pyridin-4-yl | 2-F, 3-Cl |
| 55 | Ex. 7 | H₃C-NH-C(O)-CH₂- | 2,6-di(CH₃)-pyridin-4-yl | 3-F, 4-F |
| 114 | Ex. 7 | H₃C-NH-C(O)-CH₂- | 2,6-di(CH₃)-pyridin-4-yl | 3-CF$_3$, 4-F |
| 105 | Ex. 7 | H₃C-NH-C(O)-CH₂- | 2,6-di(CH₃)-pyridin-4-yl | 3-CF$_3$, 5-OCH$_3$ |

TABLE 1-continued
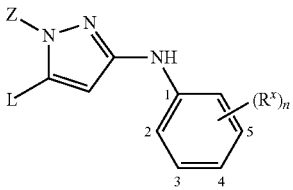
| Co. No. | Ex. No. | Z | L | R^x |
|---|---|---|---|---|
| 120 | Ex. 7 | 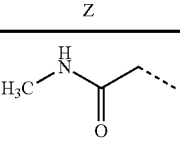 | 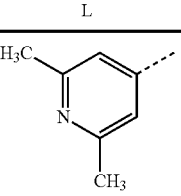 | 2-F, 3-F, 4-F |
| 127 | Ex. 7 | 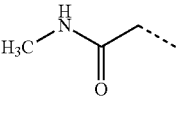 | 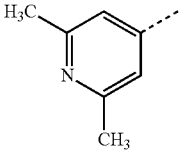 | 3-F, 4-F, 5-F |
| 155 | Ex. 7 | 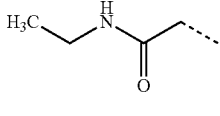 | 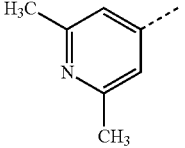 | 3-CF$_3$ |
| 139 | Ex. 7 | 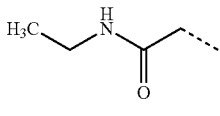 | 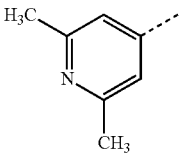 | 3-OCF$_3$ |
| 154 | Ex. 7 | 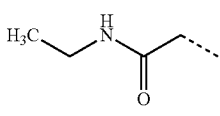 | 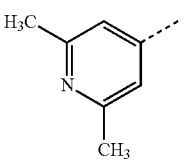 | 2-F, 3-Cl |
| 151 | Ex. 7 | 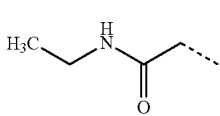 | 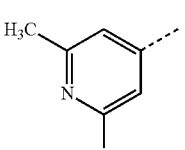 | 3-F, 4-F |
| 152 | Ex. 7 | 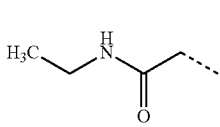 | 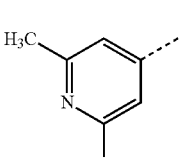 | 3-CF$_3$, 4-F |
| 140 | Ex. 7 | 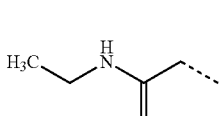 | 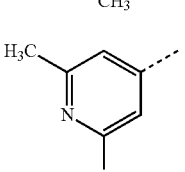 | 3-CF$_3$, 5-OCH$_3$ |

TABLE 1-continued
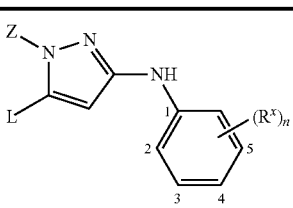
| Co. No. | Ex. No. | Z | L | R$^x$ |
|---|---|---|---|---|
| 148 | Ex. 7 | 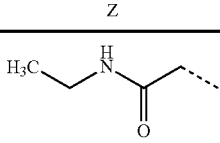 | 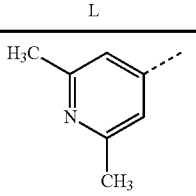 | 2-F, 3-F, 4-F |
| 167 | Ex. 7 | 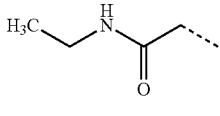 | 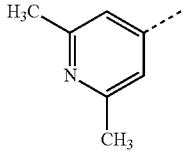 | 3-F, 4-F, 5-F |
| 150 | Ex. 7 | 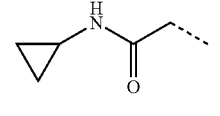 | 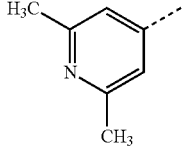 | 3-CF$_3$ |
| 147 | Ex. 7 | 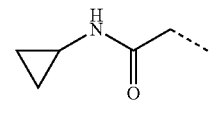 | 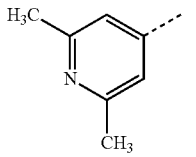 | 3-OCF$_3$ |
| 169 | Ex. 7 | 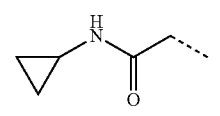 | 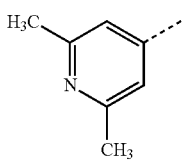 | 2-F, 3-Cl |
| 160 | Ex. 7 | 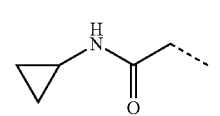 | 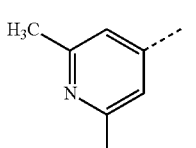 | 3-F, 4-F |
| 159 | Ex. 7 | 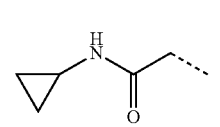 | 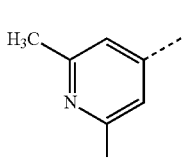 | 3-CF$_3$, 4-F |
| 138 | Ex. 7 | 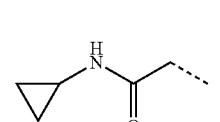 | 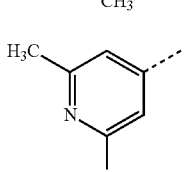 | 3-CF$_3$, 5-OCH$_3$ |

TABLE 1-continued
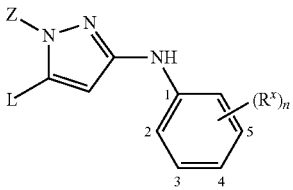
| Co. No. | Ex. No. | Z | L | R$^x$ |
|---|---|---|---|---|
| 156 | Ex. 7 | 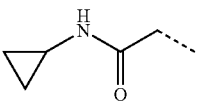 | 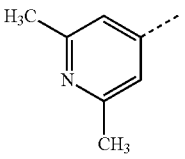 | 2-F, 3-F, 4-F |
| 172 | Ex. 7 | 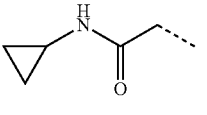 | 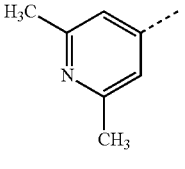 | 3-F, 4-F, 5-F |
| 100 | Ex. 7 | 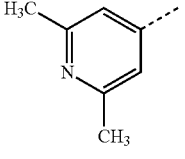 | 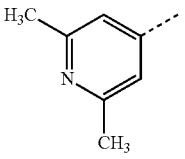 | 3-Cl |
| 57 | Ex. 7 | 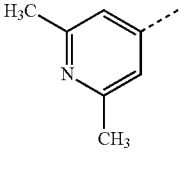 | 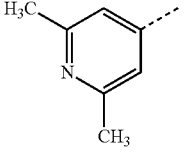 | 3-F, 4-F |
| 144 | Ex. 7 | 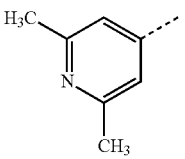 | 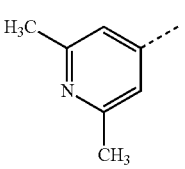 | 3-CF$_3$ |
| 180 | Ex. 7 | | | 3-OCF$_3$ |
| 175 | Ex. 7 | | | 2-F, 3-Cl |
| 171 | Ex. 7 | | | 3-F, 4-F |

TABLE 1-continued
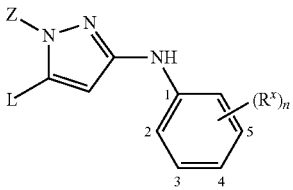
| Co. No. | Ex. No. | Z | L | R$^x$ |
|---|---|---|---|---|
| 174 | Ex. 7 | 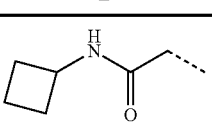 | 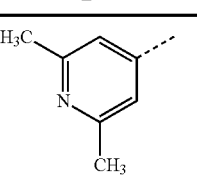 | 3-CF$_3$, 4-F |
| 162 | Ex. 7 | 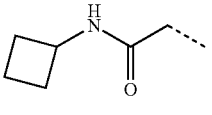 | 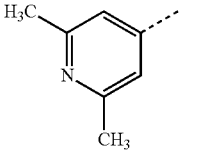 | 3-CF$_3$, 5-OCH$_3$ |
| 182 | Ex. 7 | 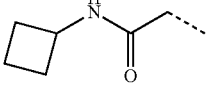 | 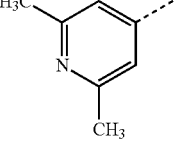 | 2-F, 3-F, 4-F |
| 179 | Ex. 7 | 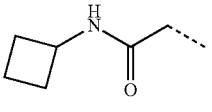 | 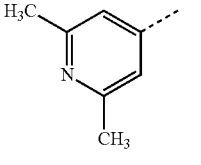 | 3-F, 4-F, 5-F |
| 56 | Ex. 1 | 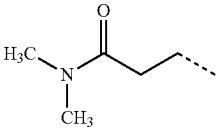 | 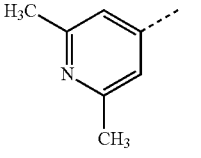 | 3-Cl |
| 178 | Ex. 1 | 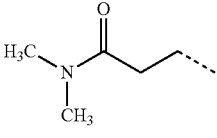 | 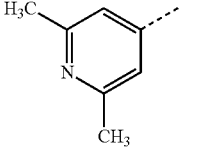 | 3-CF$_3$ |
| 165 | Ex. 1 | 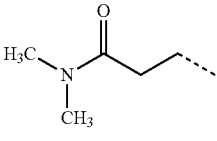 | 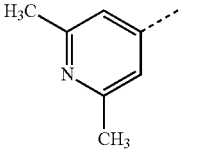 | 3-OCF$_3$ |
| 173 | Ex. 1 | 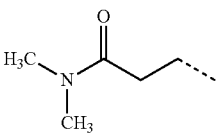 | 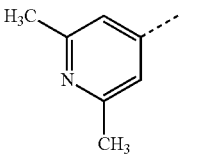 | 2-F, 3-Cl |

TABLE 1-continued
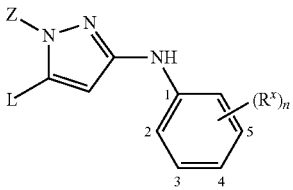
| Co. No. | Ex. No. | Z | L | Rˣ |
|---|---|---|---|---|
| 119 | Ex. 1 | 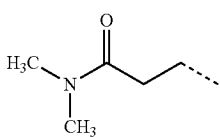 | 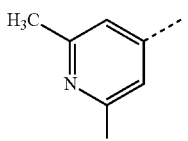 | 3-F, 4-F |
| 161 | Ex. 1 | 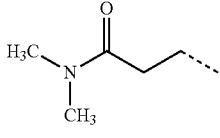 | 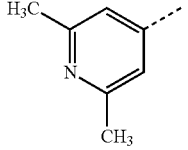 | 3-CF₃, 4-F |
| 58 | Ex. 1 | 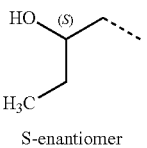<br>S-enantiomer | 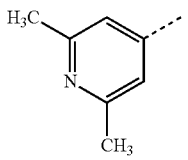 | 3-Cl |
| 59 | Ex. 1 | 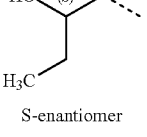<br>S-enantiomer | 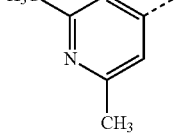 | 3-F, 4-F |
| 101 | Ex. 1 | 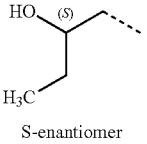<br>S-enantiomer | 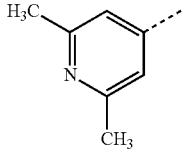 | 3-CF₃, 5-OCH₃ |
| 4 | Ex. 4 | 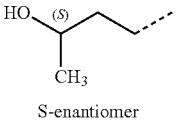<br>S-enantiomer | 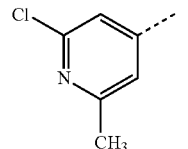 | 3-CF₃, 4-F |
| 60 | Ex. 2 | 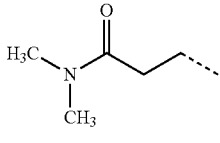 | 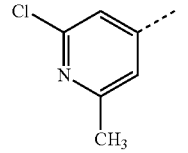 | 3-F, 4-F |
| 102 | Ex. 9 | 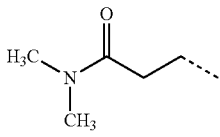 | 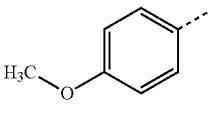 | 3-F, 4-F |

TABLE 1-continued
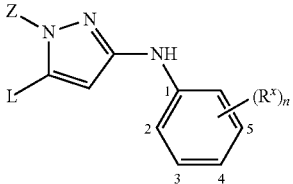
| Co. No. | Ex. No. | Z | L | Rˣ |
|---|---|---|---|---|
| 61 | Ex. 8 | 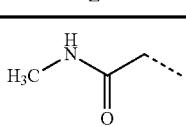 | 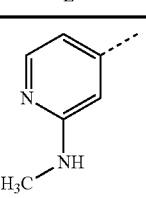 | 3-F, 4-F |
| 62 | Ex. 8 | 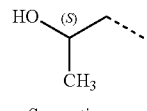<br>S-enantiomer | 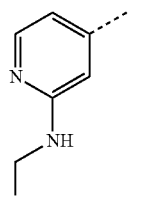 | 3-F, 4-F |
| 63 | Ex. 8 | 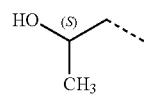<br>S-enantiomer | 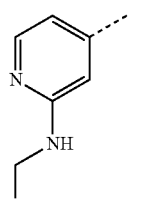 | 3-CF₃, 5-OCH₃ |
| 64 | Ex. 8 | 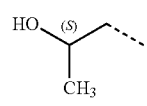<br>S-enantiomer | 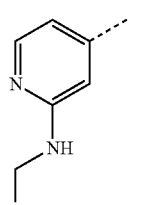 | 3-F, 5-CF₃ |
| 133 | Ex. 8 | 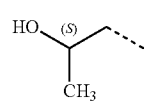<br>S-enantiomer | 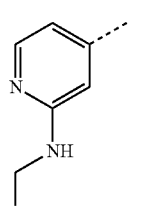 | 2-F, 3-F, 4-F |
| 65 | Ex. 8 | 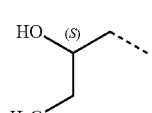<br>S-enantiomer | 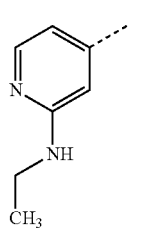 | 3-F, 4-F |

TABLE 1-continued
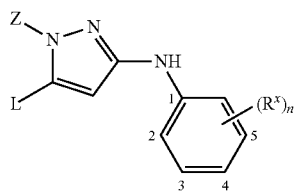
| Co. No. | Ex. No. | Z | L | R^x |
|---|---|---|---|---|
| 8 | Ex. 8 | HO-CH(S)-CH2-, H3C (S-enantiomer) | 4-pyridyl with 2-NHCH2CH3 | 3-F, 5-F |
| 135 | Ex. 8 | HO-CH(S)-CH2-, H3C (S-enantiomer) | 4-pyridyl with 2-NHCH2CH3 | 2-F, 3-F, 4-F |
| 66 | Ex. 8 | HO-CH(S)-CH3 (S-enantiomer) | 6-methyl-pyridyl with NHCH2CH3 | 3-F, 4-F |
| 67 | Ex. 8 | HO-CH(S)-CH3 (S-enantiomer) | 6-methyl-pyridyl with NHCH2CH3 | 3-CF3, 4-F |
| 68 | Ex. 8 | HO-CH(S)-CH2-, H3C (S-enantiomer) | 6-methyl-pyridyl with NHCH2CH3 | 3-CF3, 4-F |
| 69 | Ex. 8 | HO-CH(S)-CH3 (S-enantiomer) | 6-methyl-pyridyl with N(CH3)2 | 3-CF3, 4-F |

TABLE 1-continued

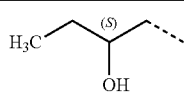

| Co. No. | Ex. No. | Z | L | Rˣ |
|---|---|---|---|---|
| 5 | Ex. 5 | (S)-CH(OH)CH₂CH₃ group, S-enantiomer | methyl pyridine-2-carboxylate, 4-linked | 3-F, 4-F |
| 177 | Ex. 7 | CH₃NHC(O)CH₂– | 2-(methoxymethyl)pyridine, 4-linked | 3-Cl |
| 149 | Ex. 1 | (CH₃)₂NC(O)CH₂CH₂– | 2-(methoxymethyl)pyridine, 4-linked | 3-Cl |
| 70 | D8 | (CH₃)₂NC(O)CH₂CH₂– | 2-(methoxymethyl)pyridine, 4-linked | 3-F, 4-F |
| 136 | Ex. 1 | (S)-CH(OH)CH₂CH₃, S-enantiomer | 2-(methoxymethyl)pyridine, 4-linked | 3-Cl |
| 113 | Ex. 1 | (S)-CH(OH)CH₂CH₃, S-enantiomer | 2-(methoxymethyl)pyridine, 4-linked | 3-CF₃ |

TABLE 1-continued
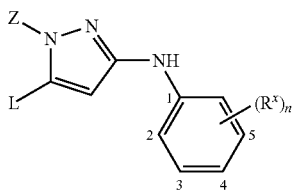
| Co. No. | Ex. No. | Z | L | R$^x$ |
|---|---|---|---|---|
| 6 | Ex. 6 | HO (S) / H$_3$C — S-enantiomer | pyridin-2-yl-CH$_2$-O-CH$_3$ (4-linked) | 3-F, 4-F |
| 71 | Ex. 6 | HO (S) / H$_3$C — S-enantiomer | pyridin-2-yl-CH$_2$-O-CH$_3$ (4-linked) | 3-F, 5-F |
| 121 | Ex. 1 | HO (S) / H$_3$C — S-enantiomer | pyridin-2-yl-CH$_2$-O-CH$_3$ (4-linked) | 2-F, 3-F, 4-F |
| 72 | Ex. 7 | H$_3$C-NH-C(O)- | 2,3-dihydro-1,4-benzodioxin-6-yl | 3-F |
| 73 | Ex. 7 | H$_3$C-NH-C(O)- | 2,3-dihydro-1,4-benzodioxin-6-yl | 4-F |
| 7 | Ex. 7 | H$_3$C-NH-C(O)- | 2,3-dihydro-1,4-benzodioxin-6-yl | 3-F, 4-F |
| 74 | Ex. 7 | H$_3$C-NH-C(O)- | 2,3-dihydro-1,4-benzodioxin-6-yl | 3-F, 4-F, 5-F |

TABLE 1-continued

| Co. No. | Ex. No. | Z | L | R$^x$ |
|---|---|---|---|---|
| 75 | Ex. 7 | H₃C-NH-C(O)- | 2,3-dihydro-1,4-benzodioxine | 3-CF₃, 4-F |
| 76 | Ex. 7 | H₃C-NH-C(O)- | 2,3-dihydro-1,4-benzodioxine | 3-CF₃ |
| 77 | Ex. 7 | H₃C-NH-C(O)- | 2,3-dihydro-1,4-benzodioxine | 3-OCF₃ |
| 78 | Ex. 7 | H₃C-CH₂-NH-C(O)- | 2,3-dihydro-1,4-benzodioxine | 3-F, 4-F, 5-F |
| 79 | Ex. 7 | H₃C-CH₂-NH-C(O)- | 2,3-dihydro-1,4-benzodioxine | 3-CF₃ |
| 80 | Ex. 7 | H₃C-CH₂-NH-C(O)- | 2,3-dihydro-1,4-benzodioxine | 3-OCF₃ |
| 81 | Ex. 7 | H₃C-CH₂-NH-C(O)- | 2,3-dihydro-1,4-benzodioxine | 3-CF₃, 4-F |
| 82 | Ex. 1 | (H₃C)₂N-C(O)-CH₂- | 2,3-dihydro-1,4-benzodioxine | 3-F |

TABLE 1-continued
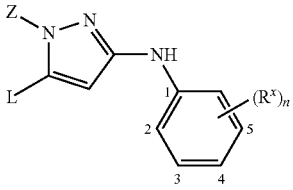
| Co. No. | Ex. No. | Z | L | R$^x$ |
|---|---|---|---|---|
| 83 | Ex. 1 | 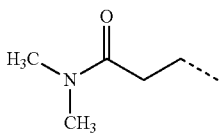 | 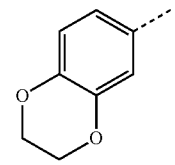 | 4-F |
| 84 | Ex. 1 | 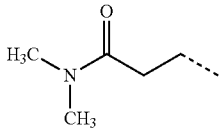 | 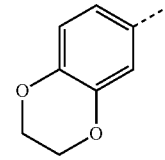 | 3-F, 4-F |
| 85 | Ex. 1 | 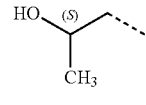 S-enantiomer | 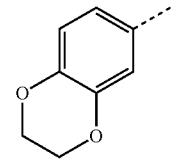 | 3-F, 4-F, 5-F |
| 10 | Ex. 10 | 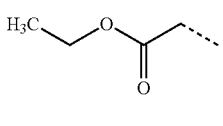 | 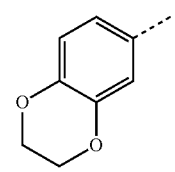 | 3-F, 4-F |
TABLE 2
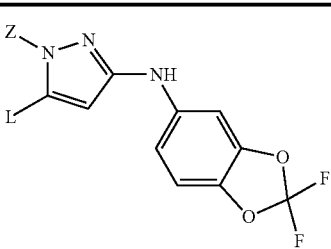
| Co. No. | Ex. No. | Z | L |
|---|---|---|---|
| 86 | Ex. 9 | 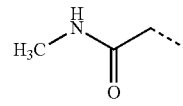 | 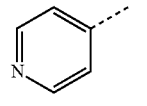 |
| 87 | Ex. 9 | 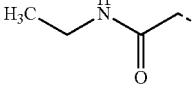 | 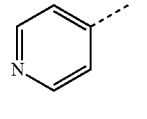 |
| 88 | Ex. 9 | 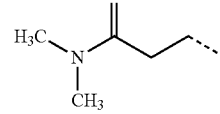 | 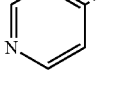 |
| 89 | Ex. 9 | 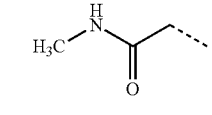 | 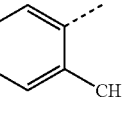 |

TABLE 2-continued

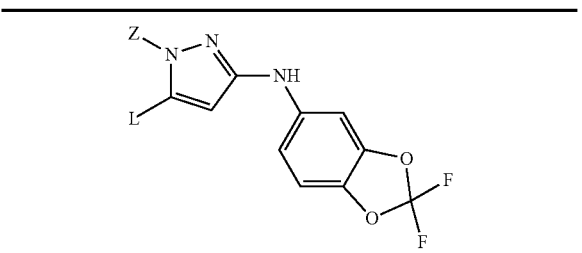

| Co. No. | Ex. No. | Z | L |
|---|---|---|---|
| 90 | Ex. 9 | H3C-N(CH3)-C(=O)-CH2CH2- | 4-pyridyl, 3-CH3 |
| 91 | Ex. 9 | H3C-CH2-NH-C(=O)-CH(-)- | 4-pyridyl, 3-CH3 |
| 92 | Ex. 7 | H3C-NH-C(=O)-CH(-)- | 4-pyridyl, 2-CH3 |
| 93 | Ex. 7 | H3C-CH2-NH-C(=O)-CH(-)- | 4-pyridyl, 2-CH3 |
| 94 | Ex. 1 | H3C-N(CH3)-C(=O)-CH2CH2- | 4-pyridyl, 2-CH3 |
| 95 | Ex. 7 | cyclopropyl-CH2-NH-C(=O)-CH(-)- | 4-pyridyl, 2-CH3 |
| 2 | Ex. 2 | H3C-N(CH3)-C(=O)-CH2CH2- | 4-pyridyl, 2-Cl |
| 112 | Ex. 7 | H3C-NH-C(=O)-CH(-)- | 4-pyridyl, 2-CH2OCH3 |

TABLE 2-continued

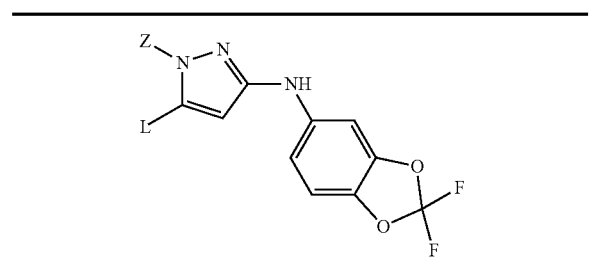

| Co. No. | Ex. No. | Z | L |
|---|---|---|---|
| 96 | Ex. 1 | H3C-N(CH3)-C(=O)-CH2CH2- | 4-pyridyl, 2-CH2OCH3 |
| 130 | Ex. 7 | H3C-NH-C(=O)-CH(-)- | 4-pyridyl, 2,6-(CH3)2 |
| 153 | Ex. 7 | H3C-CH2-NH-C(=O)-CH(-)- | 4-pyridyl, 2,6-(CH3)2 |
| 145 | Ex. 7 | cyclopropyl-NH-C(=O)-CH(-)- | 4-pyridyl, 2,6-(CH3)2 |
| 158 | Ex. 7 | cyclobutyl-NH-C(=O)-CH(-)- | 4-pyridyl, 2,6-(CH3)2 |
| 157 | Ex. 7 | H3C-N(CH3)-C(=O)-CH2CH2- | 4-pyridyl, 2,6-(CH3)2 |
| 97 | Ex. 7 | H3C-NH-C(=O)-CH(-)- | 2,3-dihydro-1,4-benzodioxin-6-yl |

TABLE 2-continued

| Co. No. | Ex. No. | Z | L |
|---|---|---|---|
| 98 | Ex. 7 | H₃C–CH₂–NH–C(=O)–CH< | 2,3-dihydro-1,4-benzodioxin-6-yl |

(Structure at top: pyrazole with Z on N1, L on C5, and NH-linked to benzo[1,3]dioxole bearing CF₂ at the 2-position)

Analytical Part
LCMS
LCMS General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with APIES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

LCMS—Method 1

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS—Method 2

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS—Method 3

In addition to general procedure B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

LCMS—Method 4

In addition to general procedure B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

LCMS—Method 5

In addition to the general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 µl was used. Cone voltage was 10 V for positive ionization mode and 20 V for negative ionization mode.

LCMS—Method 6

In addition to the general procedure C: Reversed phase HPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in H₂O/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

LCMS—Method 7

In addition to the general procedure C: Reversed phase HPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM ammonium acetate in H₂O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 30 V for positive ionization mode and 30 V for negative ionization mode.

LCMS—Method 8

In addition to the general procedure C: Reversed phase HPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used.

Cone voltage was 10 V for positive ionization mode and 20 V for negative ionization mode.

LCMS—Method 9

In addition to the general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Melting Points

For a number of compounds, melting points were determined with a DSC823e from Mettler-Toledo (indicated by superscript [a]). Melting points were measured with a temperature gradient of 30° C./minute. Values are peak values.

For a number of compounds, melting points were determined with a Diamond DSC from PerkinElmer (indicated by superscript [b]). Melting points were measured with a temperature gradient of 10° C./minute. Maximum temperature was 300° C. Values are either peak values or melt ranges (onset of peak till end of peak).

For a number of compounds, melting points were determined with a WRS-2A melting point apparatus that was purchased from Shanghai Precision and Scientific Instrument Co. Ltd. (indicated by superscript [c]). Melting points were measured with a linear heating up rate of 0.2-5.0° C./minute The reported values are melt ranges. The maximum temperature was 300° C.

TABLE 3

Analytical data - Retention time ($R_t$ in minutes), $(MH)^+$ peak, LCMS method and melting points ('m.p.' is defined as melting point and 'inc.' is defined as inconclusive).

| Co. Nr. | $R_t$ | $(MH)^+$ | LCMS Method | m.p. (° C.) |
|---|---|---|---|---|
| 1 | 1.04 | 470 | 5 | |
| 2 | 0.97 | 450 | 5 | |
| 3 | 4.95 | 402 | 1 | 177.8[a] |
| 4 | 1.05 | 443 | 5 | |
| 5 | 0.94 | 403 | 5 | |
| 6 | 5.49 | 389 | 1 | inc. |
| 7 | 4.33 | 401 | 4 | 189.5-194.5[b] |
| 8 | 5.75 | 388 | 1 | inc. |
| 9 | 5.77 | 436 | 1 | 156.7[a] |
| 10 | 5.76 | 401 | 1 | — |
| 11 | 5.80 | 435 | 1 | inc. |
| 12 | 5.98 | 435 | 1 | inc. |
| 13 | 4.77 | 376 | 3 | 140.0[b] |
| 14 | 4.89 | 392 | 3 | 146.0[b] |
| 15 | 4.52 | 362 | 3 | 242.3[b] |
| 16 | 4.72 | 358 | 1 | 208.0[a] |
| 17 | 3.91 | 406 | 4 | — |
| 18 | 3.78 | 390 | 4 | — |
| 19 | 4.90 | 372 | 1 | 164.8[a] |
| 20 | 4.73 | 358 | 1 | 229.4[a] |
| 21 | 5.37 | 372 | 1 | 172.9[a] |
| 22 | 5.47 | 386 | 1 | 162.5[a] |
| 23 | 5.89 | 436 | 1 | 146.8[a] |
| 24 | 5.60 | 345 | 1 | inc. |
| 25 | 5.97 | 395 | 1 | — |
| 26 | 5.58 | 386 | 1 | 178.3[a] |
| 27 | 5.40 | 422 | 1 | 204.7[a] |
| 28 | 5.61 | 436 | 1 | — |
| 29 | 5.83 | 409 | 1 | inc. |
| 30 | 5.39 | 408 | 1 | inc. |
| 31 | 5.58 | 422 | 1 | — |
| 32 | 3.60 | 390 | 4 | 191.4[a] |
| 33 | 5.22 | 374 | 1 | 196.8[a] |
| 34 | 3.47 | 408 | 4 | — |
| 35 | 3.62 | 406 | 4 | 173.9[b] |
| 36 | 3.54 | 404 | 4 | 142.7[b] |
| 37 | 3.63 | 420 | 4 | 150.4[b] |
| 38 | 5.39 | 422 | 1 | 163.1[a] |
| 39 | 5.44 | 388 | 1 | 193.0[a] |
| 40 | 5.14 | 386 | 1 | 141.4[a] |
| 41 | 5.65 | 402 | 1 | 162.0[a] |
| 42 | 5.65 | 361 | 1 | 195.5[a] |
| 43 | 5.62 | 395 | 1 | 168.5[a] |
| 44 | 5.49 | 363 | 1 | 189.4[a] |
| 45 | 5.46 | 359 | 1 | 137.2[a] |
| 46 | 5.88 | 409 | 1 | 215.6[a] |
| 49 | 5.70 | 409 | 1 | — |
| 50 | 5.44 | 434 | 1 | inc. |
| 51 | 5.62 | 448 | 1 | — |
| 52 | 5.80 | 462 | 1 | inc. |
| 53 | 6.00 | 435 | 1 | 154.4[a] |
| 54 | 5.16 | 370 | 1 | 187.3[a] |
| 55 | 4.95 | 372 | 1 | 222.2[a] |
| 55 | 4.95 | 372 | 1 | 222.20[a] |
| 56 | 5.59 | 398 | 1 | inc. |
| 57 | 5.48 | 412 | 1 | 201.3[a] |
| 58 | 5.89 | 371 | 1 | inc. |
| 59 | 5.69 | 373 | 1 | 144.6[a] |
| 60 | 5.67 | 420 | 1 | 124.6[a] |
| 61 | 4.73 | 373 | 1 | 204.0[a] |
| 62 | 5.38 | 374 | 1 | — |
| 63 | 5.79 | 436 | 1 | inc. |
| 64 | 5.98 | 424 | 1 | inc. |
| 65 | 5.63 | 388 | 1 | inc. |
| 66 | 5.70 | 388 | 1 | inc. |
| 67 | 6.05 | 438 | 1 | inc. |
| 68 | 6.26 | 452 | 1 | inc. |
| 69 | 6.33 | 438 | 1 | inc. |
| 70 | 5.16 | 416 | 1 | — |
| 71 | 5.56 | 389 | 1 | inc. |
| 72 | 4.24 | 383 | 4 | 189.5-194.0[b] |
| 73 | 4.18 | 383 | 4 | 169.9-177.3[b] |
| 74 | 4.47 | 419 | 4 | 215.4[b] |
| 75 | 4.59 | 451 | 4 | 223.9[b] |
| 76 | 4.54 | 433 | 4 | 183.9[b] |
| 77 | 4.69 | 449 | 4 | inc. |
| 78 | 4.60 | 433 | 4 | 206.2[b] |
| 79 | 4.66 | 447 | 4 | inc. |
| 80 | 4.62 | 463 | 4 | 153.2[b] |
| 81 | 4.69 | 465 | 4 | 169.3[b] |
| 82 | 4.42 | 411 | 4 | — |
| 83 | 4.37 | 411 | 4 | 141.6-143.2[c] |
| 84 | 4.51 | 429 | 4 | — |
| 85 | 5.98 | 406 | 1 | 160.8[a] |
| 86 | 5.01 | 388 | 1 | 178.5[a] |
| 87 | 5.22 | 402 | 1 | 178.2[a] |
| 88 | 5.12 | 416 | 2 | 212.8[a] |
| 89 | 5.15 | 402 | 1 | inc. |
| 90 | 5.52 | 430 | 1 | inc. |
| 91 | 5.36 | 416 | 1 | inc. |
| 92 | 3.41 | 402 | 4 | 166.7[b] |
| 93 | 5.41 | 416 | 1 | 186.9[a] |
| 94 | 5.57 | 430 | 1 | 184.1[a] |
| 95 | 5.67 | 442 | 1 | 215.3[a] |
| 96 | 5.57 | 460 | 1 | — |
| 97 | 4.53 | 445 | 4 | 171.5-171.8[c] |
| 98 | 4.77 | 459 | 4 | inc. |

TABLE 3-continued

Analytical data - Retention time ($R_t$ in minutes), $(MH)^+$ peak, LCMS method and melting points ('m.p.' is defined as melting point and 'inc.' is defined as inconclusive).

| Co. Nr. | $R_t$ | $(MH)^+$ | LCMS Method | m.p. (° C.) |
|---|---|---|---|---|
| 99 | 5.91 | 451 | 1 | inc. |
| 100 | 5.68 | 410 | 1 | 170.47[a] |
| 101 | 6.07 | 435 | 1 | 107.39[a] |
| 102 | 5.74 | 401 | 1 | — |
| 103 | | | | |
| 104 | 1.16 | 446 | 6 | |
| 105 | 0.97 | 434 | 7 | 205.98[a] |
| 106 | 4.82 | 404 | 2 | |
| 107 | 1.04 | 376 | 6 | |
| 108 | 1.07 | 400 | 6 | |
| 109 | 1.16 | 376 | 6 | 254.38[a] |
| 110 | 0.91 | 413 | 8 | 181.75[a] |
| 111 | 1.09 | 370 | 6 | 161.21[a] |
| 112 | 5.3 | 432 | 9 | 179.89[a] |
| 113 | 5.52 | 421 | 2 | |
| 114 | 0.96 | 422 | 7 | 202.84[a] |
| 115 | 1.03 | 455 | 5 | |
| 116 | 1.13 | 402 | 6 | |
| 117 | 0.96 | 404 | 7 | 177.05[a] |
| 118 | 1.21 | 375 | 6 | 134.50[a] |
| 119 | 5.38 | 400 | 1 | 141.04[a] |
| 120 | 0.89 | 390 | 7 | 195.27[a] |
| 121 | 5.39 | 407 | 2 | |
| 122 | 1.16 | 387 | 6 | 121.22[a] |
| 123 | 1.06 | 382 | 6 | |
| 124 | 1.11 | 402 | 6 | |
| 125 | 1.11 | 390 | 6 | 199.35[a] |
| 126 | 1.08 | 414 | 6 | |
| 127 | 0.97 | 390 | 6 | 246.52[a] |
| 128 | 1.17 | 390 | 6 | 237.19[a] |
| 129 | 1.06 | 420 | 6 | 207.14[a] |
| 130 | 1.1 | 416 | 6 | 221.70[a] |
| 131 | 1.23 | 460 | 6 | 135.65[a] |
| 132 | 1.16 | 426 | 6 | |
| 133 | 0.97 | 392 | 6 | |
| 134 | 5.85 | 377 | 9 | 137.31[a] |
| 135 | 1.08 | 406 | 6 | |
| 136 | 5.79 | 387 | 9 | 61.47[a] |
| 137 | 1.09 | 388 | 6 | 189.67[a] |
| 138 | 0.97 | 460 | 7 | 165.57[a] |
| 139 | 1.12 | 434 | 6 | 190.69[a] |
| 140 | 1.01 | 448 | 7 | |
| 141 | 0.93 | 388 | 7 | 208.22[a] |
| 142 | 1.2 | 404 | 6 | 171.37[a] |
| 143 | 1.17 | 448 | 6 | 122.33[a] |
| 144 | 1.16 | 444 | 6 | 192.53[a] |
| 145 | 0.99 | 442 | 6 | |
| 146 | 1.06 | 384 | 6 | |
| 147 | 1.12 | 446 | 6 | 25.31[a] |
| 148 | 1.00 | 404 | 6 | 180.32[a] |
| 149 | 1.2 | 414 | 6 | |
| 150 | 1.08 | 430 | 6 | 204.55[a] |
| 151 | 0.87 | 386 | 7 | 202.29[a] |
| 152 | 1.09 | 436 | 6 | 192.62[a] |
| 153 | 1.17 | 430 | 6 | 208.38[a] |
| 154 | 0.94 | 402 | 7 | 182.51[a] |
| 155 | 0.95 | 418 | 7 | 189.11[a] |
| 156 | 1.02 | 416 | 6 | 196.82[a] |
| 157 | 1.07 | 444 | 6 | 165.61[a] |
| 158 | 1.16 | 456 | 6 | |
| 159 | 1.1 | 448 | 6 | |
| 160 | 0.95 | 398 | 6 | 214.03[a] |
| 161 | 1.09 | 450 | 6 | 171.55[a] |
| 162 | 1.19 | 474 | 6 | 172.36[a] |
| 163 | 0.97 | 396 | 8 | |
| 164 | 1.3 | 416 | 6 | 172.96[a] |
| 165 | 1.13 | 448 | 6 | |
| 166 | 1.14 | 404 | 6 | 163.91[a] |
| 167 | 1.04 | 404 | 6 | 237.72[a] |
| 168 | 1.27 | 416 | 6 | 220.32[a] |
| 169 | 0.94 | 414 | 7 | 183.72[a] |
| 170 | 1.19 | 414 | 6 | |
| 171 | 0.99 | 412 | 7 | 217.50[a] |
| 172 | 1.06 | 416 | 6 | 245.41[a] |
| 173 | 1.06 | 416 | 6 | |
| 174 | 1.07 | 462 | 7 | 185.71[a] |
| 175 | 1.07 | 428 | 7 | 178.25[a] |
| 176 | 0.95 | 366 | 6 | |
| 177 | 5.06 | 386 | 9 | 175.31[a] |
| 178 | 1.12 | 432 | 6 | 127.92[a] |
| 179 | 1.16 | 430 | 6 | 243.37[a] |
| 180 | 1.20 | 460 | 6 | 191.68[a] |
| 181 | 1.16 | 434 | 6 | 177.28[a] |
| 182 | 1.12 | 430 | 6 | 196.65[a] |
| 183 | 5.92 | 421 | 9 | 121.6[a] |
| 184 | 0.97 | 389 | 8 | |
| 185 | 1.16 | 357 | 6 | |

D. Pharmacological Examples

Example D.1

$Ca^{2+}$ Flux Imaging (FDSS) (Protocol B)

Materials
a) Assay Buffer

Hanks buffered saline solution (HBSS, Invitrogen, Belgium), supplemented with 10 mM HEPES (Invitrogen, Belgium), $CaCl_2$ to a final concentration of 5 mM, 0.1% Bovine serum albumin (Sigma-Aldrich NV, Belgium).

b) Calcium-Sensitive Dye—Fluo-4AM

Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 μM.

c) 384-Well Plates

Black 384 well plate black/clear plates, PDL pre-coated (Corning, Incorporated, USA)

d) Calcium Flux Measurement

A Functional drug screening system (FDSS, Hamamatsu) was used to measure intracellular free-calcium flux signals.

Method

Monolayers of hα7-wt nAChR-expressing cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.

PAM activity was detected in real time by applying the compounds to be tested to the loaded cells along with a α7 nicotinic receptor agonist during constant monitoring of cellular fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a sub-maximal concentration of 100 μM. In a further setting of the present invention the compounds to be tested were applied prior to the α7 nicotinic receptor agonist, in a particular embodiment up to 10 minutes prior to the agonist.

A control response to choline was calculated on each plate from the difference in peak in fluorescence in wells receiving either choline or assay buffer alone. Compounds of the present invention were tested at a concentration range from 0.01 μM to 30 μM. Compounds were considered to have an interesting activity when they potentiated the choline signal at least with 200% when tested at a concentration of 30 μM (the efficacy of 100 μM choline was defined as 100% in the absence of a PAM). An $EC_{50}$ (or $pEC_{50}$) was determined as a concentration relating to half the maximal effect, when a clear sigmoidal curve with top plateau was obtained. The $EC_{50}$ (or $pEC_{50}$) was defined as lower than maximal concentration in case the compound activity did not reach a top plateau at maximal concentration (indicated in table 8 as "<5")

The compounds also have a potentiating effect on the response to choline when measured by whole-cell patch clamp electrophysiology in GH4C1 cells stably over-expressing the human wild-type α7 receptor.

Example D.2

Patch-Clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important an application system is used which is capable of very rapid switching of solutions (<100 ms) to prevent partial or full desensitisation of receptor responses coincident with the time of agonist application. Consequently, a second convenient technique to assess the enhancement of nicotinic efficacy is patch-clamp recording from hα7-wt nAChR-expressing GH4C1 cells coupled with a rapid-application system.

Materials a) Assay Buffers

The external recording solution consisted of 152 mM NaCl, 5 mM KCl, 1 mM $MgCl_2$, 1 mM Calcium, 10 mM HEPES; pH 7.3. The internal recording solution consisted of 140 mM CsCl, 10 mM HEPES, 10 mM EGTA, 1 mM $MgCl_2$, pH 7.3.

b) Patch-clamp recording was carried out using a Patch-clamp amplifier (Multiclamp 700A, Axon Instruments, CA, USA). hα7-wt nAChR-expressing GH4C1 cells were patch-clamp in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1 GΩ and series resistance <15 MΩ with at least 60% series resistance compensation. Membrane potential was clamped at −70 mV.

c) Agonists

ACh, choline, were purchased from Sigma-Aldrich NV, Belgium.

d) Compound Application

A 16-channel Dynflow DF-16 microfluidics system (Cellectricon, Sweden) for rapid switching of solutions (switching resolution time<100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 μl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist and even more particularly 5 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by compounds of the invention indicates that they are expected to have useful therapeutic activity. $EC_{50}$ values (potency), maximal effect (% efficacy), and Hill slopes were estimated by fitting the data to the logistic equation using GraphPad Prism (GraphPad Software, Inc., San Diego, Calif.).

TABLE 8

Potency ($pEC_{50}$) and % efficacy for a number of compounds. The $pEC_{50}$ and % efficacy values are those from the $Ca^{2+}$ assay as described in D.1. The PAM type is obtained from the patch clamp current recording as described herein-before).

| Co. No. | pEC50 | % Efficacy | PAM type |
|---|---|---|---|
| 6 | 5.94 | 2403 | 2 |
| 7 | 6.71 | 2900 | 2 |
| 8 | 6.02 | 1000 | 1 |
| 9 | 5.99 | 2200 | 4 |
| 10 | 6.61 | 4995 | 2 |
| 11 | 6.84 | 4194 | |
| 12 | 6.18 | 2220 | 0 |
| 13 | <5 | 967 @ 30 μM | |
| 14 | 5.29 | 1100 | |
| 15 | <5 | 832 @ 30 μM | |
| 16 | <5 | 1288 @ 30 μM | |
| 17 | <5 | 1484 @ 30 μM | |
| 18 | <5 | 592 @ 30 μM | |
| 19 | 5.37 | 2400 | 2 |
| 20 | <5 | 5091 @ 30 μM | |
| 21 | 5.91 | 3000 | 3 |
| 22 | 5.61 | 1900 | 2 |
| 23 | 6.20 | 2300 | 2 |
| 24 | 5.67 | 300 | |
| 25 | 6.03 | 500 | |
| 26 | 5.56 | 800 | |
| 27 | 5.94 | 3400 | 2 |
| 28 | 6.11 | 1400 | 4 |
| 29 | 5.95 | 500 | |
| 30 | <5 | 1748 @ 30 μM | |

TABLE 8-continued

Potency (pEC$_{50}$) and % efficacy for a number of compounds. The pEC$_{50}$ and % efficacy values are those from the Ca$^{2+}$ assay as described in D.1. The PAM type is obtained from the patch clamp current recording as described herein-before).

| Co. No. | pEC50 | % Efficacy | PAM type |
|---|---|---|---|
| 31 | 5.57 | 1500 | |
| 32 | 5.37 | 2400 | 2 |
| 33 | 5.75 | 1500 | |
| 34 | 5.47 | 1800 | |
| 35 | 5.61 | 2500 | 2 |
| 36 | 5.72 | 2200 | 2 |
| 37 | 6.00 | 2500 | |
| 38 | 6.24 | 1500 | 2 |
| 39 | 6.11 | 1500 | |
| 40 | 6.00 | 3000 | 2 |
| 41 | 6.41 | 1400 | |
| 42 | 5.95 | 200 | |
| 43 | 5.84 | 700 | 1 |
| 44 | 5.91 | 400 | |
| 45 | 5.91 | 800 | 1 |
| 46 | 6.05 | 1034 | 0 |
| 47 | 6.36 | 3449 | |
| 48 | | | |
| 49 | 5.74 | 500 | |
| 50 | 5.21 | 496 | |
| 51 | 5.48 | 1746 | 2 |
| 52 | 6.04 | 5054 | |
| 53 | 5.97 | 482 | 0 |
| 54 | 6.01 | 1651 | 2 |
| 55 | 5.77 | 3552 | 2 |
| 56 | 6.28 | 3001 | 2 |
| 57 | 6.68 | 3232 | 2 |
| 58 | 6.12 | 1479 | 1 |
| 59 | 6.21 | 1167 | 1 |
| 60 | 6.30 | 1100 | |
| 61 | <5 | 1191 @ 30 μM | |
| 62 | 5.88 | 1200 | 1 |
| 63 | 5.40 | 700 | |
| 64 | 5.85 | 500 | |
| 65 | 6.24 | 1000 | 2 |
| 66 | <5 | 2791 @ 30 μM | |
| 67 | 5.86 | 800 | |
| 68 | 6.14 | 1300 | 0 |
| 69 | 6.10 | 400 | |
| 70 | 5.87 | 4600 | 3 |
| 71 | 5.86 | 700 | 1 |
| 72 | 6.19 | 3800 | 2 |
| 73 | 6.36 | 3800 | 3 |
| 74 | 6.60 | 2400 | 2 |
| 75 | 6.66 | 2500 | |
| 76 | 6.46 | 3100 | 4 |
| 77 | 6.38 | 3300 | 4 |
| 78 | 6.52 | 3500 | |
| 79 | 6.66 | 2900 | |
| 80 | 6.69 | 3300 | |
| 81 | 6.67 | 3300 | |
| 82 | 6.87 | 1600 | |
| 83 | 6.93 | 2000 | |
| 84 | 7.29 | 2000 | |
| 85 | 5.96 | 400 | 0 |
| 86 | 5.64 | 2200 | 3 |
| 87 | 6.06 | 2700 | 3 |
| 88 | 6.51 | | |
| 89 | <5 | 2156 @ 30 μM | |
| 90 | 6.04 | 2300 | 4 |
| 91 | 5.58 | 1400 | 2 |
| 92 | 5.73 | 3700 | 2 |
| 93 | 6.00 | 3700 | 2 |
| 94 | 6.62 | 2200 | 2 |
| 95 | 6.63 | 1100 | 2 |
| 96 | 6.74 | 1700 | 3 |
| 97 | 5.95 | 3100 | |
| 98 | 6.49 | 2800 | |
| 99 | 6.02 | 3446 | |
| 100 | 6.47 | 3076 | 2 |
| 101 | 6.82 | 1421 | |
| 102 | 7.11 | 6268 | 4 |
| 103 | 6.61 | 4995 | 2 |
| 104 | 5.57 | 1101 | 3 |
| 105 | 5.5 | 1474 | |
| 106 | 5.71 | 1935 | 2 |
| 107 | 5.73 | 907 | 2 |
| 108 | 5.73 | 2523 | 2 |
| 109 | 5.75 | 559 | |
| 110 | 5.75 | 1355 | 2 |
| 111 | 5.77 | 1893 | 2 |
| 112 | 5.82 | 3938 | 4 |
| 113 | 5.88 | 1081 | |
| 114 | 5.94 | 1034 | |
| 115 | 5.9 | 516 | |
| 116 | 5.91 | 596 | |
| 117 | 5.83 | 835 | |
| 118 | 5.93 | 633 | 0 |
| 119 | 5.96 | 2560 | 2 |
| 120 | 5.94 | 969 | |
| 121 | 5.97 | 1112 | 2 |
| 122 | 5.99 | 2548 | 1 |
| 123 | 6 | 1608 | 2 |
| 124 | 6.01 | 1653 | 1 |
| 125 | 6.03 | 972 | 2 |
| 126 | 6.04 | 2506 | 2 |
| 127 | 5.99 | 616 | |
| 128 | 6.07 | 643 | 2 |
| 129 | 6.03 | 726 | |
| 130 | 6.09 | 632 | 2 |
| 131 | 6.09 | 2113 | 2 |
| 132 | 6.1 | 3602 | 2 |
| 133 | 6.11 | 409 | |
| 134 | 6.11 | 1175 | 1 |
| 135 | 6.12 | 1047 | 1 |
| 136 | 6.19 | 1486 | 1 |
| 137 | 6.2 | 946 | 2 |
| 138 | 6.21 | 686 | |
| 139 | 6.19 | 710 | |
| 140 | 6.00 | 1043 | 2 |
| 141 | 6.25 | 519 | |
| 142 | 6.21 | 816 | 2 |
| 143 | 6.24 | 2678 | 4 |
| 144 | 6.36 | 444 | |
| 145 | 6.32 | 736 | 2 |
| 146 | 6.35 | 1451 | 2 |
| 147 | 6.22 | 643 | |
| 148 | 6.33 | 1054 | |
| 149 | 6.36 | 1587 | 4 |
| 150 | 6.28 | 568 | |
| 151 | 6.26 | 749 | 2 |
| 152 | 6.33 | 856 | 2 |
| 153 | 6.38 | 737 | 2 |
| 154 | 6.28 | 901 | 2 |
| 155 | 6.26 | 576 | 2 |
| 156 | 6.42 | 975 | |
| 157 | 6.44 | 503 | 2 |
| 158 | 6.44 | 509 | 1 |
| 159 | 6.34 | 842 | |
| 160 | 6.28 | 927 | |
| 161 | 6.62 | 737 | |
| 162 | 6.36 | 750 | |
| 163 | 6.49 | 1436 | 2 |
| 164 | 6.51 | 482 | 2 |
| 165 | 6.44 | 738 | 1 |
| 166 | 6.53 | 856 | 2 |
| 167 | 6.58 | 762 | |
| 168 | 6.58 | 778 | 2 |
| 169 | 6.52 | 577 | |
| 170 | 6.73 | 783 | 2 |
| 171 | 6.83 | 507 | |
| 172 | 6.73 | 393 | |
| 173 | 6.87 | 401 | 1 |
| 174 | 6.66 | 651 | |
| 175 | 6.9 | 462 | |
| 176 | | 420 @ 30 μM | |

TABLE 8-continued

Potency (pEC$_{50}$) and % efficacy for a number of compounds. The pEC$_{50}$ and % efficacy values are those from the Ca$^{2+}$ assay as described in D.1. The PAM type is obtained from the patch clamp current recording as described herein-before).

| Co. No. | pEC50 | % Efficacy | PAM type |
|---|---|---|---|
| 177 | | 2054 @ 30 μM | |
| 178 | 6.26 | 627 | |
| 179 | 6.94 | 793 | |
| 180 | 6.43 | 768 | |
| 181 | | 4093 @ 30 μM | 2 |
| 182 | 6.74 | 1242 | |
| 183 | 6.1 | 1819 | 0 |
| 184 | 5.94 | 721 | 1 |
| 185 | 5.8 | 1286 | 1 |

The invention claimed is:

1. A compound according to formula (I)

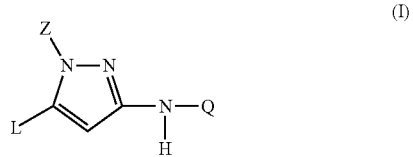

(I)

or a stereochemically isomeric form thereof, wherein

Z is $C_{1-6}$alkyl substituted with one or more substituents independently selected from the group consisting of hydroxyl, $R^1R^2N$—C(=O)—, $R^3O$—C(=O)— and halo;

Q is 2,2-difluorobenzodioxol-5-yl, unsubstituted phenyl or phenyl substituted with one, two or three substituents independently selected from the group consisting of halo, hydroxyl, cyano, $C_{1-6}$alkyl, $C_{1-6}$alkyl-O—, polyhalo$C_{1-6}$alkyl and polyhalo$C_{1-6}$alkyl-O—;

L is phenyl, pyridinyl or benzodioxanyl, each optionally substituted with one, two or more substituents independently selected from the group consisting of halo, cyano, $C_{1-6}$alkyl, $C_{1-6}$alkyl-O—, $C_{1-6}$alkyl-S—, polyhalo$C_{1-6}$alkyl, polyhalo$C_{1-6}$alkyl-O—, mono- and di($C_{1-6}$alkyl)amino, pyrrolidinyl, piperidinyl, morpholinyl, $CH_3O$—$C_{1-6}$alkyl-NH—, HO—$C_{1-6}$alkyl-NH—, $C_{3-6}$cycloalkyl, $C_{3-6}$cycloalkyl-NH—, $C_{3-6}$cycloalkyl-$C_{1-6}$alkyl-NH—, $C_{1-6}$alkyl-O—$C_{1-6}$alkyl-, methoxycarbonyl and $C_{3-6}$cycloalkyl-O—$C_{1-6}$alkyl-;

$R^1$ and $R^2$ each independently represent hydrogen, $C_{1-6}$alkyl, $C_{3-6}$cycloalkyl, $C_{1-4}$-alkyl-O—$C_{1-6}$alkyl or $C_{3-6}$cycloalkyl$C_{1-6}$alkyl; or $R^1$ and $R^2$ taken together with the nitrogen atom to which they are attached form a heterocyclic radical selected from the group consisting of pyrrolidinyl, piperidinyl, and morpholinyl, each optionally substituted with one, two or three substituents each independently selected from the group consisting of halo, hydroxy and $C_{1-6}$alkyl;

$R^3$ is hydrogen or $C_{1-3}$alkyl; or a pharmaceutically acceptable addition salt, or a hydrate or a solvate thereof.

2. The compound according to claim 1 wherein

Z is $C_{1-4}$alkyl substituted with hydroxyl or $R^1R^2N$—C(=O)—;

Q is 2,2-difluorobenzodioxol-5-yl, phenyl substituted with one, two or three substituents independently selected from the group consisting of halo, trifluoromethyl, trifluoromethoxy, and methoxy;

L is phenyl substituted with one or two substituents selected from the group consisting of halo and methoxy; pyridinyl substituted with one, two or three substituents selected from the group consisting of halo, methyl, $C_{1-2}$alkylamino, $C_{1-2}$alkyloxycarbonyl, and $C_{1-2}$alkyloxy$C_{1-2}$alkyl; or benzodioxanyl;

$R^1$ and $R^2$ each independently represent hydrogen, methyl, ethyl, cyclopropyl or cyclopropylmethyl; or $C_{3-6}$cycloalkyl$C_{1-3}$alkyl; or a pharmaceutically acceptable addition salt, or a hydrate or a solvate thereof.

3. The compound according to claim 1, wherein

L is pyridinyl substituted with one or two substituents selected from the group consisting of halo, methyl, $C_{1-2}$alkylamino, $C_{1-2}$alkyloxycarbonyl, and $C_{1-2}$alkyloxy$C_{1-2}$alkyl; or benzodioxanyl;

$R^1$ and $R^2$ each independently represent hydrogen, methyl, ethyl, cyclopropyl, cyclobutyl or cyclopropylmethyl; or a pharmaceutically acceptable addition salt, or a hydrate or a solvate thereof.

4. The compound according to claim 1, wherein

Z is (2S)-2-hydroxypropyl, (2S)-2-hydroxybutyl, $(CH_3)_2N$—C(=O)—$CH_2$—$CH_2$—, $CH_3NH$—C(=O)—$CH_2$—, $C_2H_5NH$—C(=O)—$CH_2$—, c.$C_3H_5NH$—C(=O)—$CH_2$—, c.$C_3H_5$—$CH_2$—NH—C(=O)—$CH_2$—, or c.$C_4H_7NH$—C(=O)—$CH_2$—, Q is 2,2-difluorobenzodioxol-5-yl, phenyl substituted with one, two or three substituents independently selected from the group consisting of fluoro, chloro, trifluoromethyl, trifluoromethoxy, and methoxy;

L is 4-pyridinyl substituted with one or two substituents selected from the group consisting of chloro, methyl, methylamino, ethylamino, dimethylamino, methoxycarbonyl and methoxymethyl;

or a pharmaceutically acceptable addition salt, or a hydrate or a solvate thereof.

5. The compound according to claim 1, wherein

Z is (2S)-2-hydroxypropyl, (2S)-2-hydroxybutyl, $(CH_3)_2N$—C(=O)—$CH_2$—$CH_2$—, $CH_3NH$—C(=O)—$CH_2$—, $C_2H_5NH$—C(=O)—$CH_2$—, c.$C_3H_5NH$—C(=O)—$CH_2$—, c.$C_3H_5$—$CH_2$—NH—C(=O)—$CH_2$—, or c.$C_4H_7NH$—C(=O)—$CH_2$—, Q is 2,2-difluorobenzodioxol-5-yl, phenyl substituted with one, two or three substituents independently selected from the group consisting of fluoro, chloro, trifluoromethyl, trifluoromethoxy, and methoxy;

L is 4-methoxyphenyl or benzodioxanyl;

or a pharmaceutically acceptable addition salt, or a hydrate or a solvate thereof.

6. A pharmaceutical composition comprising a pharmaceutically acceptable carrier and as active ingredient a therapeutically effective amount of a compound as claimed in claim 1.

7. A process of preparing a pharmaceutical composition comprising mixing a pharmaceutically acceptable carrier with a therapeutically effective amount of a compound as claimed in claim 1.

* * * * *